(12) United States Patent
Chen et al.

(10) Patent No.: US 12,364,411 B2
(45) Date of Patent: *Jul. 22, 2025

(54) DIAGNOSIS OF RESPIRATORY DISEASES USING ANALYSIS OF EXHALED BREATH AND AEROSOLS

(71) Applicant: Zeteo Tech, Inc., Sykesville, MD (US)

(72) Inventors: Dapeng Chen, Sykesville, MD (US); Wayne A. Bryden, Sykesville, MD (US); Michael McLoughlin, Sykesville, MD (US)

(73) Assignee: Zeteo Tech, Inc., Sykesville, MD (US)

( * ) Notice: Subject to any disclaimer, the term of this patent is extended or adjusted under 35 U.S.C. 154(b) by 6 days.

This patent is subject to a terminal disclaimer.

(21) Appl. No.: 18/532,476

(22) Filed: Dec. 7, 2023

(65) Prior Publication Data
US 2024/0115157 A1 Apr. 11, 2024

Related U.S. Application Data

(63) Continuation of application No. 17/916,649, filed as application No. PCT/US2020/048035 on Aug. 26, 2020, now Pat. No. 11,839,463.
(Continued)

(51) Int. Cl.
| | |
|---|---|
| *A61B 5/08* | (2006.01) |
| *A61B 5/097* | (2006.01) |
| *G01N 33/497* | (2006.01) |

(52) U.S. Cl.
CPC ............ *A61B 5/082* (2013.01); *A61B 5/097* (2013.01); *G01N 33/497* (2013.01)

(58) Field of Classification Search
None
See application file for complete search history.

(56) References Cited

U.S. PATENT DOCUMENTS

| | | | |
|---|---|---|---|
| 6,062,392 A | 5/2000 | Birmingham et al. | |
| 6,267,016 B1 | 7/2001 | Call et al. | |
| (Continued) | | | |

FOREIGN PATENT DOCUMENTS

| | | |
|---|---|---|
| EP | 3336543 A1 | 6/2018 |
| EP | 2823300 B1 | 10/2019 |
| (Continued) | | |

OTHER PUBLICATIONS

International Preliminary Report on Patentability (with Annex) for PCT/US2023/029760 dated Oct. 8, 2024 by IPEA/KR.
(Continued)

*Primary Examiner* — Jay B Shah
(74) *Attorney, Agent, or Firm* — Paradice and Li LLP; Anand S. Chellappa

(57) ABSTRACT

Methods and devices for analyzing non-volatile organics in exhaled breath and other aerosols using various diagnostic tools that enable rapid, low-cost point of care assays for several diseases including respiratory tract diseases such as COVID-19. The disclosed methods and systems selectively capture non-volatile organics in exhaled breath and other aerosols in a packed bed column. The non-volatile organics are eluted and samples are analysis using diagnostic devices including MALDI-TOFMS. The disclosed systems and methods provide for a diagnostic test result in less than about 20 minutes and provides for autonomous operation with minimal human intervention.

21 Claims, 9 Drawing Sheets

Related U.S. Application Data

(60) Provisional application No. 63/069,029, filed on Aug. 22, 2020, provisional application No. 63/010,029, filed on Apr. 14, 2020, provisional application No. 63/005,179, filed on Apr. 3, 2020.

(56) References Cited

U.S. PATENT DOCUMENTS

| | | | |
|---|---|---|---|
| 7,779,840 | B2 | 8/2010 | Acker et al. |
| 8,409,870 | B2 | 4/2013 | Van Wuijckhuijse et al. |
| 8,424,523 | B2 | 4/2013 | Ogilvie et al. |
| 8,434,481 | B2 | 5/2013 | Ogilvie et al. |
| 8,434,483 | B2 | 5/2013 | Patel et al. |
| 8,944,059 | B2 | 2/2015 | Mansour et al. |
| 9,022,029 | B2 | 5/2015 | Varga et al. |
| 9,089,665 | B2 | 7/2015 | Patel |
| 9,675,773 | B2 | 6/2017 | Colman et al. |
| 10,632,276 | B2 | 4/2020 | Fyfe et al. |
| 10,926,052 | B2 | 2/2021 | Colman et al. |
| 11,135,392 | B2 | 10/2021 | Oddo et al. |
| 11,229,763 | B2 | 1/2022 | Oddo et al. |
| 11,246,506 | B2 | 2/2022 | Gunneson et al. |
| 11,359,733 | B2 | 6/2022 | Oddo et al. |
| 11,400,250 | B2 | 8/2022 | Oddo et al. |
| 11,547,322 | B2 | 1/2023 | Lundin et al. |
| 11,617,848 | B2 | 4/2023 | Fyfe et al. |
| 11,826,512 | B2 | 11/2023 | Oddo et al. |
| 11,896,366 | B2 | 2/2024 | Cardin |
| 2003/0208132 | A1 | 11/2003 | Baddour |
| 2005/0137491 | A1 | 6/2005 | Paz et al. |
| 2007/0068811 | A1 | 3/2007 | Tsukashima et al. |
| 2008/0038207 | A1 | 2/2008 | Edwards et al. |
| 2009/0156952 | A1 | 6/2009 | Hunter et al. |
| 2012/0172679 | A1 | 7/2012 | Logan et al. |
| 2013/0217029 | A1 | 8/2013 | Sislian et al. |
| 2013/0327122 | A1 | 12/2013 | Dutta et al. |
| 2016/0020080 | A1 | 1/2016 | Pyun et al. |
| 2016/0022946 | A1 | 1/2016 | Sislian et al. |
| 2016/0231333 | A1 | 8/2016 | Sutherland |
| 2017/0035326 | A1 | 2/2017 | King-Smith |
| 2017/0119280 | A1 | 5/2017 | Ahmad et al. |
| 2017/0299477 | A1 | 10/2017 | Milton et al. |
| 2017/0303822 | A1 | 10/2017 | Allsworth et al. |
| 2018/0246120 | A1 | 8/2018 | Bryden et al. |
| 2019/0000351 | A1 | 1/2019 | Scampoli |
| 2019/0094195 | A1 | 3/2019 | Gentner |
| 2019/0282124 | A1 | 9/2019 | Wu et al. |
| 2020/0147333 | A1 | 5/2020 | Stoll et al. |
| 2020/0345266 | A1 | 11/2020 | Schleich |
| 2021/0321903 | A1 | 10/2021 | Daniels |
| 2021/0345956 | A1 | 11/2021 | Keays et al. |
| 2021/0386959 | A1 | 12/2021 | Oddo et al. |
| 2022/0183587 | A1 | 1/2022 | Karshmer |
| 2022/0323045 | A1 | 10/2022 | Chen et al. |
| 2022/0370751 | A1 | 11/2022 | Oddo et al. |
| 2022/0381766 | A1 | 12/2022 | Cardin |
| 2023/0172484 | A1 | 6/2023 | Lundin et al. |
| 2023/0256189 | A1 | 8/2023 | Fyfe et al. |

FOREIGN PATENT DOCUMENTS

| | | | |
|---|---|---|---|
| JP | H0989863 | A | 4/1997 |
| JP | H09126958 | A | 5/1997 |
| JP | H10227725 | A | 8/1998 |
| JP | 2011102747 | A | 5/2011 |
| JP | 5848608 | B2 | 1/2016 |
| JP | 2019184288 | A | 10/2019 |
| JP | 2020534511 | A | 11/2020 |
| KR | 1020160130229 | | 11/2016 |
| WO | 2004090534 | A1 | 10/2004 |
| WO | 2009045163 | A1 | 4/2009 |
| WO | 2017197386 | A1 | 11/2017 |
| WO | 2019011750 | A1 | 1/2019 |
| WO | 2019145678 | A1 | 8/2019 |
| WO | 2021061330 | A1 | 4/2021 |
| WO | 2021201905 | A1 | 10/2021 |

OTHER PUBLICATIONS

"Ventilator/Ventilator Support, What to Expect," NIH, National Heart, Lung, and Blood Institute, downloaded from the internet on Jul. 8, 2024 at <https://www.nhlbi.nih.gov/health/ventilator/what-to-expect#:~:text=Ventilators>, 7-pages, last updated Mar. 24, 2022.

Guise M T et al: "An experimental investigation of aerosol collection utilizing packed beds of silica aerogel microspheres", Journal of Non-Crystalline Solids, North-Holland Physics Publishing. Amsterdam, NL, vol. 285, No. 1-3, Jun. 1, 2001 (Jun. 1, 2001), pp. 317-322, XP004242941, ISSN: 0022-3093, DOI: 10.1016/S0022-3093(01)00473-2. (Year: 2001).

International Search Report and Written Opinion for PCT/US2020/048035, issued by ISA/KIPO on Dec. 30, 2020.

Written Opinion of ISA/KIPO for PCT/US2020/048040 issued Dec. 9, 2020.

International Preliminary Report on Patentability (with Annex) for PCT/US2020/048035, mailed Mar. 22, 2022 by IPEA/KR.

Hunt, J., "Exhaled breath condensate: An evolving tool for noninvasive evaluation of lung disease," J. Allergy Clin. Immunol. 2002; 110:28-34.

Benjamin Patterson, Carl Morrow, Vinayak Singh, Atica Moosa, Melitta Gqada, Jeremy Woodward, Valerie Mizrahi, Wayne Bryden, Charles Call, Shwetak Patel, Digby Warner, Robin Wood, "Detection of *Mycobacterium tuberculosis* bacilli in bio-aerosols from untreated TB patients," Gates Open Research 2018, 1:11.

B. Bake, P. Larsson, G. Ljungkvist, E. Ljungström, and A-C Olin, "Exhaled particles and small airways," Respiratory Research (2019) 20:8.

Fennelly K.P., Martyny J.W., Fulton K.E., Orme I.M., Cave D.M., et al. (2004) Cough-generated aerosols of *Mycobacterium tuberculosis*: a new method to study infectiousness. Am J Respir Crit Care Med 169: 604-609.

Dina Hashoul and Hossam Haick, "Sensors for detecting pulmonary diseases from exhaled breath," Eur. Respir. Rev. 2019; 28: 190011.

Maria D. King, Andrew R. McFarland, "Bioaerosol Sampling with a Wetted Wall Cyclone: Cell Culturability and DNA Integrity of *Escherichia coli* Bacteria," Aerosol Sci. Technol., 46:82-93, 2012.

James J. McDevitt, Petros Koutrakis, Stephen T. Ferguson, Jack M. Wolfson, M. Patricia Fabian, Marco Martins, Jovan Pantelic, and Donald K. Milton, "Development and Performance Evaluation of an Exhaled-Breath Bioaerosol Collector for Influenza Virus," Aerosol Sci. Technol. Jan. 1, 2013; 47(4): 444-451.

Wood R., Morrow C., Barry C.E., III, Bryden W.A., Call C.J., Hickey A.J., et al.: Real-Time Investigation of Tuberculosis Transmission: Developing the Respiratory Aerosol Sampling Chamber (RASC). PLoS One. 2016; 11(1): e0146658.

Rachel C. Wood, Angelique K. Luabeya, Kris M. Weigel, Alicia K. Wilbur, Lisa Jones-Engel, Mark Hatherill, and Gerard A. Cangelosi, "Detection of *Mycobacterium tuberculosis* DNA on the oral mucosa of tuberculosis patients," Sci. Rep. 5, 8668 (2015).

Fatima B. Wurie, Stephen D. Lawn, Helen Booth, Pam Sonnenberg, Andrew C. Hayward, "Bioaerosol production by patients with tuberculosis during normal tidal breathing: implications for transmission risk," Thorax 2016; 71: 549-554.

International Search Report and Written Opinion of ISA/KIPO for PCT/US2022/022964 dated Jul. 13, 2022.

International Preliminary Report on Patentability (with Annex) for PCT/US2022/022964 dated May 11, 2023 by IPEA/KR.

International Search Report and Written Opinion of ISA/KIPO for PCT/US2023/029760 dated Nov. 24, 2023.

Chen et al., "A Novel System for the Comprehensive Collection of Nonvolatile Molecules from Human Exhaled Breath," Journal of Breath Research, vol. 15, No. 1, Oct. 20, 2020 (Oct. 20, 2020), p. 016001, XP09328706.

Chen et al., 'Noninvasive Proteomic Markers for Respiratory Tract Infections in Mechanically Ventilated Patients', medRxiv, Aug. 18,

(56) References Cited

OTHER PUBLICATIONS

2022, [retrieved on Jan. 18, 2025]. Retrieved from <URL: https://www.medrxiv.org/content/10.1101/2022.08.17.22278888v1>, pp. 3, 7, and figure 1.
International Search Report and Written Opinion of ISA/KIPO for PCT/US2024/052658 dated Feb. 6, 2025.
Khamchun et al., 'Coronin-1A serves as a serum biomarker for supportive diagnosis of *Mycobacterium tuberculosis* infection', Germs, Mar. 2023, pp. 20-31, [retrieved on Jan. 18, 2025]. Retrieved from <URL: https://pmc.ncbi.nlm.nih.gov/articles/PMC10659747>, p. 22 and table 1.
Song et al., 'Proteomic Profiling of Serum from Patients with Tuberculosis', Ann Lab Med 2014, 34(5), pp. 345-353, [retrieved on Jan. 18, 2025]. Retrieved from <URL: https://doi.org/10.3343/alm.2014.34.5.345>, p. 347 and table 1.

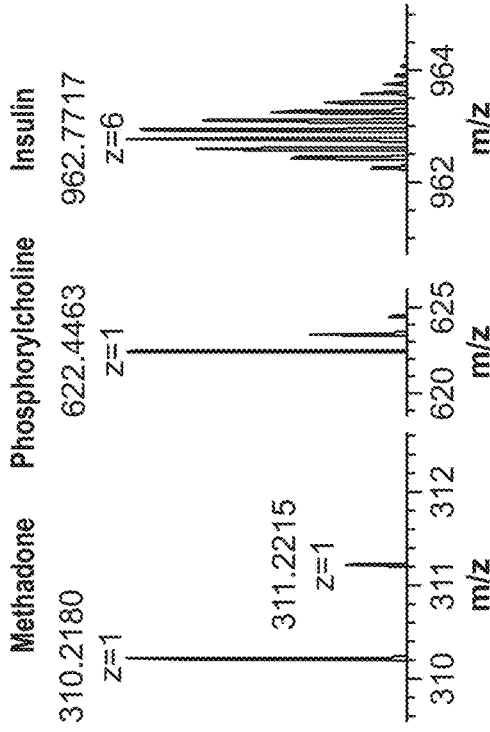
FIG. 5A
FIG. 5B
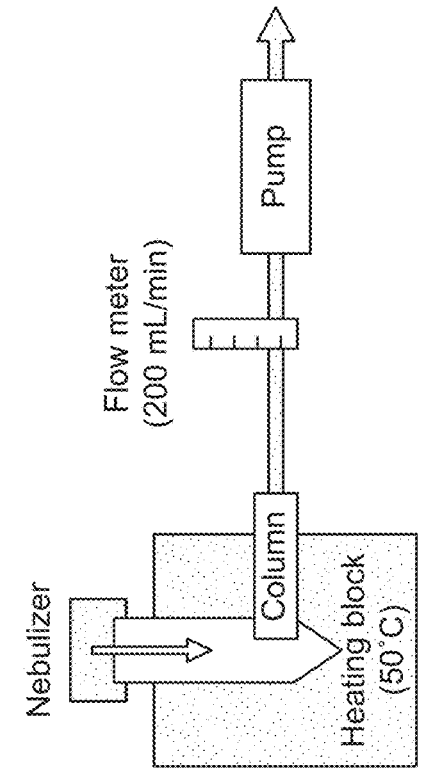
FIG. 5C
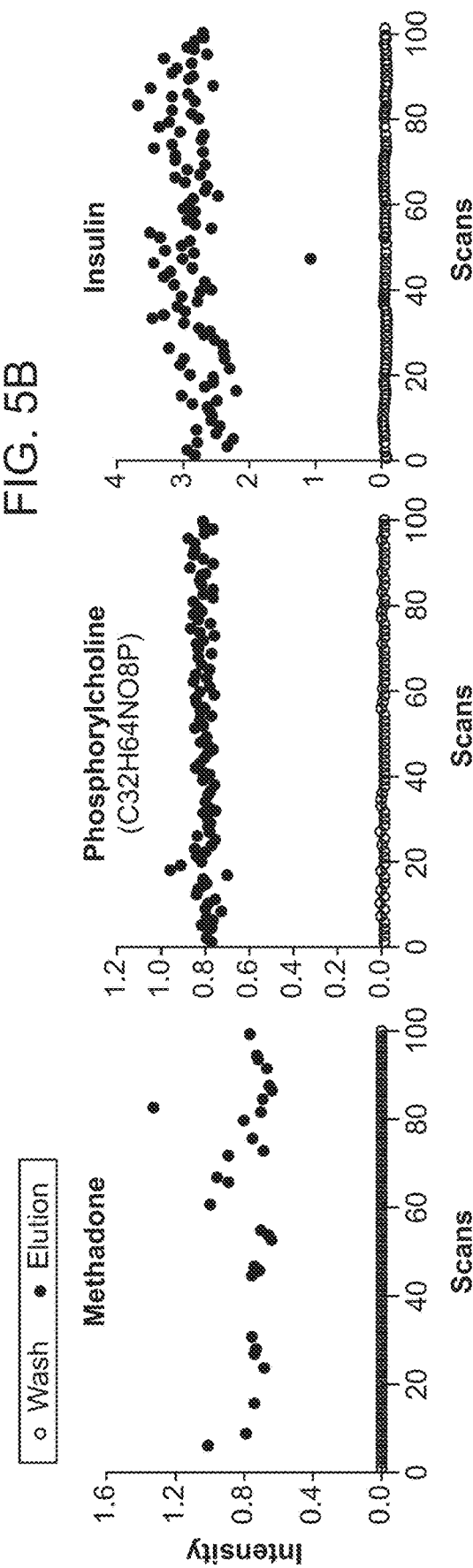
FIG. 5D
FIG. 5E

DIAGNOSIS OF RESPIRATORY DISEASES USING ANALYSIS OF EXHALED BREATH AND AEROSOLS

RELATED APPLICATIONS

This application is a continuation of U.S. patent application Ser. No. 17/916,649, filed Oct. 3, 2022, and titled "DIAGNOSIS OF RESPIRATORY DISEASES USING ANALYSIS OF EXHALED BREATH AND AEROSOLS," which is a U.S. National Stage Application of International Patent Appl. No. PCT/US2020/048035, filed Aug. 26, 2020, and titled "DIAGNOSIS OF RESPIRATORY DISEASES USING ANALYSIS OF EXHALED BREATH AND AEROSOLS," which is related to and claims the benefit of U.S. Provisional Patent Appl. No. 63/005,179, filed Apr. 3, 2020, and titled "Diagnosis of Respiratory Diseases Using Exhaled Breath," U.S. Provisional Patent Appl. No. 63/010,029, filed Apr. 14, 2020, and titled "Diagnosis of Respiratory Diseases Using Exhaled Breath," and U.S. Provisional Patent Appl. No. 63/069,029, filed Aug. 22, 2020, and titled "Diagnosis of Respiratory Diseases Using Analysis of Exhaled Breath and Aerosols," the entire disclosures of which are hereby incorporated herein by reference in each of their respective entireties.

FEDERALLY SPONSORED RESEARCH AND DEVELOPMENT

None.

FIELD

This disclosure relates to methods and devices for analyzing non-volatile organics in exhaled breath and other aerosols using various diagnostic tools to enable rapid, low cost and autonomous point of care assays for respiratory tract diseases. More particularly, but not by way of limitation, the present disclosure relates to methods and devices for analyzing non-volatile organics in exhaled breath and other to detect respiratory diseases such as COVID-19 and tuberculosis diagnosis using mass spectromtery, including MALDI-TOFMS.

BACKGROUND

Coronavirus Disease (COVID-19) is a disease caused by the newly emerged coronavirus SARS-CoV-2. This new coronavirus is a respiratory virus and spreads primarily through droplets generated when an infected person coughs or sneezes, or through droplets of saliva or discharge from the nose. The novel coronavirus is highly contagious and has created an ongoing COVID-19 pandemic which suggests that this virus is spreading more rapidly than influenza. To help in mitigation, rapid detection tools are needed.

Further, tuberculosis (TB) has surpassed HIV/AIDS as a global killer with more than 4000 daily deaths. (Patterson, B., et al., 2018). The rate of decline in incidence remains inadequate at a reported 1.5% per annum and it is unlikely that treatment alone will significantly reduce the burden of disease. In communities with highly prevalent HIV, *Mycobacterium tuberculosis* (Mtb) genotyping studies have found that recent transmission, rather than reactivation, accounts for the majority (54%) of incident TB cases. The physical process of TB transmission remains poorly understood and the application of new technologies to elucidate key events in infectious aerosol production, release, and inhalation, has been slow. Empirical studies to characterize airborne infectious particles have been sparse. Two major difficulties plaguing investigation are the purportedly low concentrations of naturally produced Mtb particles, and the complication of environmental and patient derived bacterial and fungal contamination of airborne samples. There have nonetheless been a number of attempts at airborne detection. A 2004 proof of concept study and subsequent feasibility study in Uganda sampled cough-generated aerosols from pulmonary TB patients. Coughing directly into a sampling chamber equipped with two viable cascade impactors resulted in positive cultures from more than a quarter of participants despite their having received 1-6 days of chemotherapy. A follow-up work employing the same apparatus found that participants with higher aerosol bacillary loads could be linked to greater household transmission rates and development of disease findings which suggest that quantitative airborne sampling may serve as a clinically relevant measure of infectivity. Therefore, interruption of transmission would likely have a rapid, measurable impact on TB incidence.

The best method to control transmission of tuberculosis is to promptly identify and treat active TB cases. (Wood, R. C., et al., 2015). Diagnosis of pulmonary TB is usually done by microbiological, microscopic, or molecular analysis of patient sputum. The "gold standard" test for TB infection in most of the developing world is a smear culture based on a sputum sample. The sample is smeared onto a culture plate, a stain is added that is specific to Mtb, and the stained cells are counted using a microscope. If the concentration of cells in the smear is greater than a set threshold, then the sample is classified as positive. If the TB counts are below this threshold, it is classified as negative. Diagnosis may take several hours. The need for sputum as a diagnostic sample is a limiting factor due to the challenges of collecting it from patients and to its complex composition. The viscosity of the material restricts test sensitivity, increases sample-to-sample heterogeneity, and increases costs and labor associated with testing.

Moreover, sputum production (which requires coughing) is an occupational hazard for healthcare workers. Sputum has several drawbacks as a sample medium. First, only about 50% of patients can provide a good sputum sample. For example, children under about age of eight often are not able to produce a sample upon request, usually because they have not developed an ability to "cough up" sputum from deep in their throat. The elderly and ill may not have the strength to cough up sputum. Others simply may not have sputum in their throat. Thus, a diagnostic method based on sputum analysis may not provide a diagnosis in as many as 50% of the patients who are in need of diagnosis. Sputum is also not useful as a diagnostic sample if it is collected one to two days after a person has been treated with antibiotics because the sample is no longer representative of the disease state deep in the lungs, and within several days after treatment begins, the number of live Mtb in the sputum is significantly reduced. Urine and blood have been proposed as sample media for the diagnosis of TB infection. Blood is highly invasive and entails the higher cost of handling blood samples that are often HIV positive since, in some parts of the world, many TB patients also have HIV co-infections. Further, a patient with an active TB infection may not have many TB cells circulating in their blood. Urine-based diagnostics have also been proposed, but these tests look for biomarkers of the disease other than living TB bacilli and have not been validated for widespread clinical use.

A sample that is easier, safer, and more uniform to collect and handle would simplify TB diagnosis. Exhaled breath contains aerosols ("EBA") and vapors that can be collected noninvasively and analyzed for characteristics to elucidate physiologic and pathologic processes in the lung. (Hunt, 2002). To capture the breath for assay, exhaled air is passed through a condensing apparatus to produce an accumulation of fluid that is referred to as exhaled breath condensate ("EBC"). Although predominantly derived from water vapor, EBC has dissolved within its nonvolatile compounds, including cytokines, lipids, surfactant, ions, oxidation products, and adenosine, histamine, acetylcholine, and serotonin. In addition, EBC traps potentially volatile water-soluble compounds, including ammonia, hydrogen peroxide, ethanol, and other volatile organic compounds. EBC has readily measurable pH. EBC contains aerosolized airway lining fluid and volatile compounds that provide noninvasive indications of ongoing biochemical and inflammatory activities in the lung. Rapid increase in interest in EBC has resulted from the recognition that in lung disease, EBC has measurable characteristics that can be used to differentiate between infected and healthy individuals. These assays have provided evidence of airway and lung redox deviation, acid-base status, and degree and type of inflammation in acute and chronic asthma, chronic obstructive pulmonary disease, adult respiratory distress syndrome, occupational diseases, and cystic fibrosis. Characterized by uncertain and variable degrees of dilution, EBC may not provide precise assessment of individual solute concentrations within native airway lining fluid. However, it can provide useful information when concentrations differ substantially between health and disease or are based on ratios of solutes found in the sample.

Patterson et al. (2018) used a custom-built respiratory aerosol sampling chamber (RASC), a novel apparatus designed to optimize patient-derived exhaled breath aerosol sampling, and to isolate and accumulate respirable aerosol from a single patient. Environmental sampling detects the Mtb present after a period of ageing in the chamber air. 35 newly diagnosed, GeneXpert (Cepheid, Inc., Sunnyvale, CA) sputum-positive, TB patients were monitored during one-hour confinement in the RASC chamber which has a volume of about 1.4 $m^3$. The GeneXpert genetic assay is based on polymerase chain reaction (PCR) and may be used to analyze a sample for TB diagnosis and to indicate whether or not there are drug resistance genes in the TB sample. The GeneXpert PCR assay for TB can accept a sputum sample and provide a positive or negative result in about one hour. The chamber incorporated aerodynamic particle size detection, viable and non-viable sampling devices, real-time C02 monitoring, and cough sound-recording. Microbiological culture and droplet digital polymerase chain reaction (ddPCR) were used to detect Mtb in each of the bio-aerosol collection devices. Mtb was detected in 77% of aerosol samples and 42% of samples were positive by mycobacterial culture and 92% were positive by ddPCR. A correlation was found between cough rate and culturable bioaerosol. Mtb was detected on all viable cascade impactor stages with a peak at aerosol sizes 2.0-3.5 μm. This suggests a median of 0.09 CFU/litre of exhaled air for the aerosol culture positives and an estimated median concentration of $4.5\times10^7$ CFU/ml of exhaled particulate bio-aerosol. Mtb was detected in bioaerosols exhaled by a majority of the untreated TB-patients using the RASC chamber. Molecular detection was found to be more sensitive that Mtb culture on solid media.

Mtb can be identified in EBA by culture, ddPCR, electron microscopy, immunoassay, and cell staining (e.g., oramine and dmn-Tre). Of these, PCR and immunoassays have the potential to be rapid and specific to the species level. PCR and other genomics-based techniques can be specific to the strain level. Mass spectrometry has also been shown to be specific to the strain level for cultures obtained from bacterial infections. For example, the Biotyper from Bruker Daltonics (Germany), has been shown to be able to identify up to 15,000 strains of bacteria that cause infections in humans. These techniques have been shown to be capable of identifying TB infection from EBA. Immunoassays for Mtb detection, such as the one based on lipoarabinomannan, are also well known.

In the case of TB, people infected with TB are often diagnosed through passive case finding when individuals present themselves to clinics. Active case finding ("ACF") is generally considered to include other methods of reaching people suspected of TB infection outside of the primary health care system. According to WHO, ACF is "systematic identification of people with suspected active TB, using tests, examinations, or other procedures that can applied rapidly." The goal of ACF is to get those infected to treatment earlier, reducing the average period of infection, and thereby reducing the spread of the disease. In the case of TB, by the time an individual goes to a clinic for help, that person may have transmitted the TB infection to between about 10 other people and about 115 other people. ACF can help to reduce or prevent significant TB transmission. The diagnostic systems and methods such as sputum analysis and blood analysis are either not automated and autonomously operated, or not rapid. Many have expensive assays that are consumed for each analysis, and thus, do not have general utility for active case finding, particularly in developing and under-developed countries. As previously described, EBA analysis appears to be a compelling diagnostic tool for TB detection that provides for rapid analysis, portability, and low cost because the need for expensive assays and consumables are eliminated. McDevitt et al. (2013) have report EBA analytical devices and methods for influenza diagnosis. An impactor is used to remove large particles (>4 μm) from exhaled breath, followed by a wetted-film collector for the smaller particles (<4 μm). The two size bins of collected particles were analyzed for influenza virus using a genomics-based method, reverse transcriptase polymerase chain reaction (rt-PCR). PCR technology uses biomolecular probes, combined with other biomolecules including enzymes, to amplify a specific sequence of DNA if that particular sequence is present in the sample. The targeted sequences are believed to be specific to the disease being identified. McDevitt et al. showed that EBA samples can be used to diagnose influenza.

The disclosed devices and methods have several shortcomings from a practical standpoint. First, the breath aerosol sample is collected into discrete samples that are several milliliters in volume, and thus, considerable effort is needed to concentrate the sample. Further, the diagnostic device is not coupled to or integrated with the sample collector and is not amenable for use as an ACF tool. The ability to automate the RNA assays to create an autonomous diagnostic tool for TB analysis is not clear. A method to determine whether sufficient volume of cough or breath aerosol was generated by a particular patient is not described. As a result, if a sample is found to be negative for influenza it may be due to a false negative resulting from inadequate sample collection. It is well known that there are large variabilities among humans with respect to the volume of aerosolized lung fluid produced during various breathing maneuvers.

The GeneXpert Ultra is a state-of-the-art genomics-based point of care diagnostic device which uses PCR technology. It may be integrated with an EBA sample collection method to perform ACF of TB and other respiratory diseases, but the sample collection times would be too long to be practical. Patterson et al. have shown that between 20 and 200 TB bacilli are typically produced in EBA and can be collected over a one-hour sampling period. A minimum of one hour of sampling would be required to use the GeneXpert Ultra as a diagnostic assay. The GeneXpert may be integrated with a system that samples air to analyze air samples for airborne pathogens. The BDS system (Northup Grumman, Edgewood, MD), is being used for screening US Postal Service mail for bacterial spores that cause anthrax as the mail passes through distribution centers. It combines a wetted-wall cyclone with a GeneXpert PCR system to autonomously sample air and report if pathogens are present. However, the GeneXpert Ultra assay has a relatively high cost per test and takes approximately an hour to complete the assay and provide a result. In general, PCR-based diagnostics are unsuitable for TB screening for ACF applications due to both the extended time needed for sampling and analysis, and the relatively high cost per test.

The time associated with a diagnostic assay is a critical parameter for a fielded, or "point of care" test. ACF is an example of a fielded diagnostic assay because, by definition, ACF takes place outside the healthcare system. In the U.S., a point-of-care test needs to provide an answer in 20 minutes or less. If not, the test is considered to be too slow and not acceptable for achieving short patient wait-times. In the developing world, and especially in countries with a history of TB prevalence, the GeneXpert may be used to provide diagnosis in about one hour. As previously described, this assay is expensive to implement on a "cost per test" basis, and therefore it is not yet widely deployed. Because of high-cost, it is not used to screen patients who appear healthy (non-symptomatic) but might have TB infection, but rather, is used to confirm a diagnosis that is strongly suspected based on other tests or factors.

Fennelly et al. (2004) described TB analysis using cough aerosol and a collection chamber that contains two Anderson cascade impactors using individuals who were known to have active patients. Individuals were asked to provide two discrete five-minute bursts of intense coughing. Culturing of impacted samples took 30-60 days, and therefore this approach is not amenable to automation. A challenging aspect of EBA as a clinical sample is the relatively small sample of volume of exhaled particulates that can be collected from breath. Further, a significant fraction of the mass collected is water. The molecules that contain diagnostic information ("biomarkers") are present in nanoliter or picogram quantities. Subsequently, the aerosol collection method must be effective in capturing a large fraction of the biomass in the exhaled breath. Exhaled breath includes air that is exhaled from the lungs through any number of maneuvers, including tidal breathing, deep breathing, coughing, and sneezing. Particular types of deep breathing maneuvers such as forced vital capacity (FVC), may be used to measure the maximum volume of lung capacity by breathing in as much as possible, and exhaling as far (or as deep) as possible to maximize the volume of exhaled breath. Forced expiratory volume (FEV) measures how much air a person can exhale during a forced breath. The amount of air exhaled may be measured during the first (FEV1), second (FEV2), and/or third seconds (FEV3) of the forced breath. Forced vital capacity (FVC) is the total amount of air exhaled during an FEV test. Forced expiratory volume and forced vital capacity are lung function tests that are measured during spirometry. Forced expiratory volume is an important measurement of lung function.

Although research has shown that respiratory diseases can be detected from breath aerosol and breath condensate, modern clinical tests for infections or diseases such as tuberculosis, influenza, pneumonia continue to utilize sputum, blood, or nasal swabs. Exhaled breath analytical tools have not been commercialized because methods and devices to efficiently collect and concentrate the trace amounts of analyte present in exhaled breath are lacking. Furthermore, there is no standard or methodology to assess how much exhaled breath is sufficient for a particular diagnosis. The disclosed example devices and methods overcome these limitations by collecting exhaled breath aerosol and breath condensate at high flow rate, high efficiency, and into relatively concentrated samples. Further, size sorting of aerosol can be incorporated to increase the signal to noise ratio for specific analytes prior to collection of the analytes. The concentrated samples may then be analyzed by several methods, but preferably, using methods that are sensitive, rapid, and highly specific to the analytes of interest. More preferably, the analysis will be rapid, and near real-time. Mass spectrometry, real-time PCR, and immunoassays have the highest potential to be sensitive, specific and nearly real-time.

A need exists for sample collection methods that can be coupled with fast diagnostic tools such as mass spectrometry ("MS") that is more rapid and reliable than sputum analysis and less invasive than blood analysis to provide a diagnostic assay that is fast, sensitive, specific and preferably, characterized by low cost per test. Such a system could be used for active case finding (ACF) of TB and other lung or respiratory tract diseases. To be effective, a system for ACF must be rapid and inexpensive on a "per diagnosis" basis. Low cost-per-test is a requirement for screening a large number of individuals to proactively prevent TB transmission to search for the few that are indeed infected with TB. Low-cost devices and methods would also be required for point-of-care diagnosis of influenza and other pathogenic viruses because patients probably infected with a "common cold" may be infected with rhinovirus. In some cases, the respiratory infection will be driven by a bacterial or fungal microbe and may be treatable with antibiotics. In other cases, the microbe may be resistant to antibiotics, and a diagnostic method that can identify microbial resistance to antibiotics is preferable. Rapid EBA methods for distinguishing between viral and bacterial infections in the respiratory tract are desired while minimizing the occurrence of false negatives due to an insufficient sample volume. Mass spectrometry, genomics methods including PCR, and immunoassays have the highest potential to be sensitive and specific. Mass spectrometry, and in particular, MALDI time-of-flight mass spectrometry (MALDI-TOFMS), is a preferred diagnostic tool for analysis EBA and EBC samples because it has been demonstrated to be sensitive, specific and near real-time.

Brief Disclosure

In some implementations, a breath sample collection system for diagnosis of a respiratory disease using exhaled breath may include a breath collection element configured to receive an individual's face for collecting exhaled breath including water, volatile organic components (VOCs) and non-volatile organic components, a sample capture element including a packed bed column to selectively capture the non-volatile organic components and removably and fluidly connected to the breath collection element and a pump in fluid communication with the sample capture element and configured to draw exhaled breath into the sample capture element. The non-volatile components in exhaled breath may include breath aerosol particles including at least one of microbes, virus, metabolite biomarkers, lipid biomarkers, and proteomic biomarkers characteristic of the respiratory disease. The example disclosed system may further includes a flow splitter disposed between the breath collection element and the sample capture element to divide the flow of exhaled breath such that a first portion of the flow is directed to the sample capture element and a second portion of the flow is directed to a HEPA filter. The system may further include a one-way valve disposed downstream of the sample capture element and disposed to be in an open position under a flow exiting from the sample capture element towards the pump and disposed to be in a closed position otherwise. The system may further include a large particle trap (first trap) including large particles of breath condensate from reaching the packed sample capture element. The size of the large particles in the large particle trap may be at least about 10 microns. The packed bed column may include solid particles including at least one of resins, cellulose, silica, agarose, and hydrated $Fe_3O_4$ nanoparticles.

The packed bed column may include resin beads having octadecyl acrylate (C18) functional groups on the surface. The resin beads may have a nominal diameter of between about 12 μm and about 20 μm. The resin beads may be packed between two porous polymeric frit discs. The polymeric frit disc disposed at the inlet end of the packed bed column may be characterized by average pore size of at least 35 μm. The polymeric frit disc disposed at the outlet end of the packed bed column may be characterized by an average pore size of about 10 μm. The weight of the packed bed may about 25 mg. The pump may be a diaphragm pump. The nominal flow rate (pull rate) of the pump may be between about 200 ml/min and about 600 ml/min. The breath extraction element may include at least one of a CPR rescue mask, a CPAP mask, a ventilator mask, and a nebulizer mouthpiece. The system may further include a second trap disposed between the sample capture element and the pump and configured to trap exhaled breath condensate (EBC) including at least one of water vapor, volatile organic components and non-volatile organic components that pass through the packed bed. The second trap may be cooled to below ambient temperature. The solid particles include functional groups immobilized on the surface of the particles wherein the functional groups include at least one of C18 (octadecyl), octyl, ethyl, cyclohexyl, phenyl, cyanopropyl, aminopropyl, 2,3-dihydroxypropoxypropyl, trimethyl-aminopropyl, carboxypropyl, benzenesulfonic acid, propylsulfonic acid, an ion exchange phase, a polymer phase, antibodies, glycans, lipids, DNA and RNA. The ion exchange phase may include at least one of diethylaminoethyl cellulose, QAE Sephadex, Q sepharose, and carboxymethyl cellulose. The polymer phase includes at least one of polystyrene-co-1,4-divinylbenzene, methacrylates, polyvinyl alcohol, starch, and agarose. The antibodies may include at least one of anti-human albumin, anti-Influenza A virus NP and Anti-SARS-CoV-2 virus. The antibodies may be immobilized on protein A/G agarose beads. The capture element may be cooled to a temperature at or below ambient temperature. The breath sample collection system may further include a humidifier disposed upstream of the inlet to the capture element to humidify exhaled breath and increase the humidity in the packed bed column.

In some implementations, a breath sample collection system for diagnosis of a respiratory disease using exhaled breath may include a breath collection element configured to receive an individual's face for collecting exhaled breath including water, volatile organic components (VOCs) and non-volatile organic components, at least one sample capture element disposed in parallel to each other when the system includes more than one element, each element including a packed bed column to selectively capture the non-volatile organic components and removably and fluidly connected to the breath extraction component, and at least one a pump in fluid communication with the at least one sample capture element and configured to draw exhaled breath into the at least one sample capture element. The nominal flow rate of the at least one pump may be about 2.5 liters/min. In one aspect, when more than multiple sample capture elements are disposed in parallel to each other each of these capture elements is fluidly connected to its own pump.

In some implementations, a sample capture element for diagnosis of a respiratory disease using exhaled breath may include a packed bed column to selectively capture non-volatile organic components in breath wherein the packed bed column including solid particles including at least one of resins, cellulose, silica, agarose, and hydrated $Fe_3O_4$ nanoparticles functional groups immobilized on the surface of the particles wherein the functional groups include at least one of C18 (octadecyl), octyl, ethyl, cyclohexyl, phenyl, cyanopropyl, aminopropyl, 2,3-dihydroxypropoxypropyl, trimethyl-aminopropyl, carboxypropyl, benzenesulfonic acid, propylsulfonic acid, ion exchange phases, polymer phases, antibodies, glycans, lipids, DNA and RNA. The solid particles may have a nominal diameter of between about 12 μm and about 20 μm. The solid particles may be packed between two porous polymeric frit discs. The polymeric frit disc disposed at the inlet end of the packed bed column may be characterized by average pore size of at least 35 μm. The polymeric frit disc disposed at the outlet end of the packed bed column may be characterized by an average pore size of about 10 μm. The ion exchange phase may include at least one of diethylaminoethyl cellulose, QAE Sephadex, Q sepharose, and carboxymethyl cellulose. The polymer phase includes at least one of polystyrene-co-1,4-divinylbenzene, methacrylates, polyvinyl alcohol, starch, and agarose. The antibodies may include at least one of anti-human albumin, anti-Influenza A virus NP and anti-SARS-CoV-2 virus antibody. The antibodies may be immobilized on protein A/G agarose beads.

In some implementations, a system for diagnosis of a respiratory disease using exhaled breath, the system may include a breath sample collection system including a breath collection element configured to receive an individual's face for collecting exhaled breath including water, volatile organic components (VOCs) and non-volatile organic components, a sample capture element including a packed bed column to selectively capture the non-volatile organic components and removably and fluidly connected to the breath extraction component, and a pump in fluid communication with the sample capture element and configured to draw exhaled breath into the sample capture element, a sample extraction system to extract non-volatile organics from the packed bed column, and a sample analysis system including a sample processing system for treating and concentrating the collected sample on a sample plate and a diagnostic device for analyzing the sample. The diagnostic device may include at least one of PCR, rt-PCR, mass spectrometer (MS), MALDI-MS, ESI-MS, and MALDI-TOFMS. The diagnostic device includes MALDI-TOFMS. The extraction system may include means to flush the pack bed column with a solvent and remove the solvent including non-volatile organics from the packed bed. The solvent may include at least one of acetonitrile, methanol, acid, isopropanol, the remaining being water. The solvent may include between about 50 vol.-% and about 70 vol. % acetonitrile in water. The solvent may include between about 50 vol.-% and about 70 vol. % isopropanol in water. The system may include between about 50 vol.-% and about 70 vol. % methanol in water. The extraction system may include means to flush the pack bed column with at least one of about 12.5% acetic acid, about 70% isopropanol, about 5% TFA, about 5% formic acid and about 10% HCl.

In some implementations, a system for diagnosis of a respiratory disease caused by a virus including at least on SARS-CoV, MERS-CoV and SARS-CoV-2 using exhaled breath may include a breath sample collection system including a breath collection element configured to receive an individual's face for collecting exhaled breath including water, volatile organic components (VOCs) and non-volatile organic components, a sample capture element including a packed bed column to selectively capture the non-volatile organic components and removably and fluidly connected to the breath extraction component, and a pump in fluid communication with the sample capture element and configured to draw exhaled breath into the sample capture element, a sample extraction system to extract non-volatile organics from the packed bed column, a sample processing system including means for hot acid digestion of non-volatile organics including virus particles extracted from the sample extraction system to generate a peptide sample characteristic of the virus, and a diagnostic device for analyzing the peptide sample. The extraction system may include means to flush the pack bed column with at least one of about 12.5% acetic acid, about 70% isopropanol, about 5% TFA, about 5% formic acid and about 10% HCl. The packed bed column may include solid particles having functional groups immobilized on the surface of the particles wherein the functional groups include at least one of glycan, heparin, heparan sulfate, and carbohydrates such as dextran.

In some implementations, a method for diagnosis of a respiratory disease caused by a virus including at least on SARS-CoV, MERS-CoV and SARS-CoV-2 by using exhaled breath may include collecting a breath sample from an individual the step including providing a breath collection element configured to receive an individual's face for collecting exhaled breath including water, volatile organic components (VOCs) and non-volatile organic components, and drawing exhaled breath into a sample capture element including a packed bed column to selectively capture the non-volatile organic components using a pump, extracting non-volatile organics including virus particles from the packed bed column using with at least one of about 12.5% acetic acid, about 70% isopropanol, about 5% TFA, about 5% formic acid, and about 10% HCl in a sample extraction system, digesting the extracted non-volatile organics to generate a peptide sample characteristic of the virus, and analyzing the peptide sample using a diagnostic device. The analyzing step may include plating the peptide sample on a MALDI matrix coated sample plate and analyzing the plated sample using MALDI-TOFMS. The packed bed column may include solid particles having functional groups immobilized on the surface of the particles wherein the functional groups include at least one of glycan, heparin, heparan sulfate, and carbohydrates such as dextran.

In some implementations, a breath sample collection system for diagnosis of at least one respiratory disease using exhaled breath may include a mask configured to receive an individual's face for collecting exhaled breath including water, volatile organic components (VOCs) and non-volatile organic components wherein the mask includes a stem and port disposed below the stem, a HEPA filter removably and fluidly connected to the stem of the mask, a sample capture element including a packed bed column to selectively capture the non-volatile organic components in exhaled breath and removably and fluidly connected to the port, and a pump in fluid communication with the sample capture element and configured to draw exhaled breath into the sample capture element. The non-volatile components in exhaled breath may include breath aerosol particles including at least one of microbes, viruses, metabolite biomarkers, lipid biomarkers, and proteomic biomarkers characteristic of the respiratory disease. The packed bed column may include solid particles including at least one of resins, cellulose, silica, agarose, and hydrated $Fe_3O_4$ nanoparticles. The packed bed column may include resin beads having C18 functional groups on the surface. The resin beads may have a nominal diameter of between about 12 µm and about 20 µm. The resin beads may be packed between two porous polymeric frit discs. The solid particles may include functional groups immobilized on the surface of the particles wherein the functional groups include at least one of C18 (octadecyl), octyl, ethyl, cyclohexyl, phenyl, cyanopropyl, aminopropyl, 2,3-dihydroxypropoxypropyl, trimethyl-aminopropyl, carboxypropyl, benzenesulfonic acid, propylsulfonic acid, an ion exchange phase, a polymer phase, antibodies, glycans, lipids, DNA and RNA. The system may further include a trap disposed between the sample capture element and the pump and configured to trap exhaled breath condensate (EBC) including at least one of water vapor, volatile organic components and non-volatile organic components that pass through the packed bed. The trap may be cooled to below ambient temperature. The solid particles may include functional groups immobilized on the surface of the particles wherein the functional groups include at least one of C18 (octadecyl), octyl, ethyl, cyclohexyl, phenyl, cyanopropyl, aminopropyl, 2,3-dihydroxypropoxypropyl, trimethyl-aminopropyl, carboxypropyl, benzenesulfonic acid, propylsulfonic acid, an ion exchange phase, a polymer phase, antibodies, glycans, lipids, DNA and RNA.

In some implementations, an example sample collection system for collecting aerosol particles for diagnosis of at least one respiratory disease may include a sample capture element including a packed bed column to selectively capture the non-volatile organic components in the aerosol, and a pump in fluid communication with the sample capture element and configured to draw the aerosol into the sample capture element. The non-volatile components in the aerosol may include at least one of microbes, virus, metabolite biomarkers, lipid biomarkers, and proteomic biomarkers characteristic of the respiratory disease. The packed bed column may include solid particles including at least one of resins, cellulose, silica, agarose, and hydrated $Fe_3O_4$ nanoparticles. The packed bed column may include resin beads having C18 functional groups on the surface. The resin beads may have a nominal diameter of between about 12 µm and about 20 µm.

In some implementations, an example system for diagnosis of a respiratory disease caused by aerosolized bacteria and virus particles may include an example sample collection system disclosed herein, a sample extraction system to extract non-volatile organics from the packed bed column, and a diagnostic device to analyze the extracted non-volatile organics sample. The extraction system may include means to flush the pack bed column with at least one of about 12.5% acetic acid, about 5% TFA, about 70% isopropanol, about 5% formic acid, and about 10% HCl. The diagnostic device may include at least one of PCR, ELISA, rt-PCR, mass spectrometer (MS), MALDI-MS, ESI-MS, and MALDI-TOFMS. The system may further include a sample processing system for treating and concentrating the collected sample on a sample plate. The sample processing system may include mixing the sample with a MALDI matrix and applying the mixed sample and MALDI matrix to a sample plate. The sample processing system may further include the step of drying the sample plate after applying the mixed sample and MALDI matrix to the sample plate. The sample processing system may include means for hot acid digestion of non-volatile organics including virus particles extracted from the sample extraction system to generate a peptide sample characteristic of the virus, mixing the peptide sample with a MALDI matrix, and, applying the mixed sample and MALDI matrix to a sample plate. The system may further include the step of drying the sample plate after applying the mixed sample and MALDI matrix to the sample plate. The MALDI matrix may include α-Cyano-4-hydroxycinnamic acid, acetonitrile, TFA and water. The aerosolized virus particles may include at least one of SARS-CoV, MERS-CoV, and SARS-CoV-2.

Other features and advantages of the present disclosure will be set forth, in part, in the descriptions which follow and the accompanying drawings, wherein the preferred aspects of the present disclosure are described and shown, and in part, will become apparent to those skilled in the art upon examination of the following detailed description taken in conjunction with the accompanying drawings or may be learned by practice of the present disclosure. The advantages of the present disclosure may be realized and attained by means of the instrumentalities and combinations particularly pointed out in the appendant claims.

DRAWINGS

The foregoing aspects and many of the attendant advantages of this disclosure will become more readily appreciated as the same becomes better understood by reference to the following detailed description, when taken in conjunction with the accompanying drawings, wherein:

FIGS. 5A-5E show the results of nonvolatile organic molecules collected using an example packed bed column and analyzed using mass spectrometry, according to some implementations.

Figure 1:
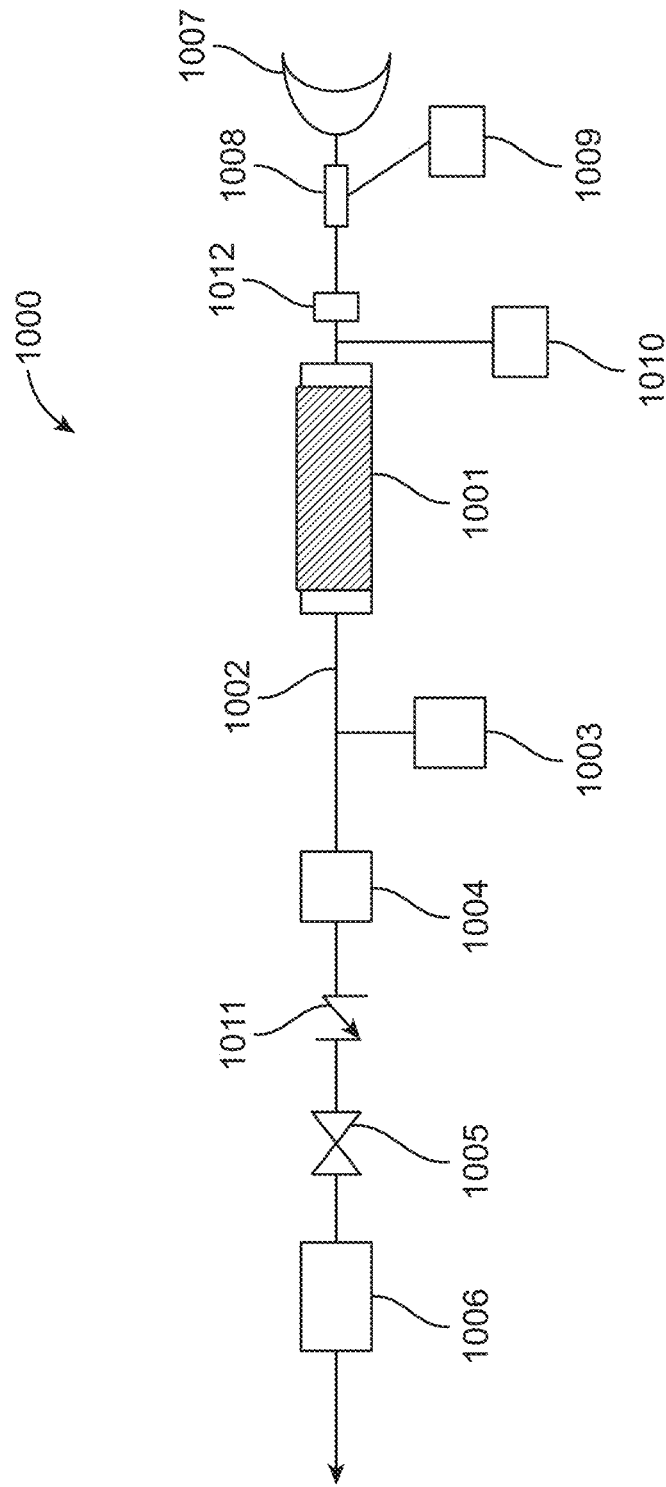
FIG. 1 shows a schematic diagram of an example exhaled breath sample collection system including a packed bed column, according to some implementations.

All reference numerals, designators and callouts in the figures are hereby incorporated by this reference as if fully set forth herein. The failure to number an element in a figure is not intended to waive any rights. Unnumbered references may also be identified by alpha characters in the figures and appendices.

The following detailed description includes references to the accompanying drawings, which form a part of the detailed description. The drawings show, by way of illustration, specific embodiments in which the disclosed systems and methods may be practiced. These embodiments, which are to be understood as "examples" or "options," are described in enough detail to enable those skilled in the art to practice the present invention. The embodiments may be combined, other embodiments may be utilized, or structural or logical changes may be made, without departing from the scope of the invention. The following detailed description is, therefore, not to be taken in a limiting sense and the scope of the invention is defined by the appended claims and their legal equivalents.

In this disclosure, aerosol generally means a suspension of particles dispersed in air or gas. "Autonomous" diagnostic systems and methods mean generating a diagnostic test result "with no or minimal intervention by a medical professional." The U.S. FDA classifies medical devices based on the risks associated with the device and by evaluating the amount of regulation that provides a reasonable assurance of the device's safety and effectiveness. Devices are classified into one of three regulatory classes: class I, class II, or class III. Class I includes devices with the lowest risk and Class III includes those with the greatest risk. All classes of devices as subject to General Controls. General Controls are the baseline requirements of the Food, Drug and Cosmetic (FD&C) Act that apply to all medical devices. In vitro diagnostic products are those reagents, instruments, and systems intended for use in diagnosis of disease or other conditions, including a determination of the state of health, in order to cure, mitigate, treat, or prevent disease or its sequelae. Such products are intended for use in the collection, preparation, and examination of specimens taken from the human body. The example devices disclosed herein can operate and produce a high-confidence result autonomously, and consequently, have the potential to be regulated as a Class I device. In some regions of the world with high burdens of TB infection, access to medically trained personnel is very limited. An autonomous diagnostic system is preferred to one that is not autonomous.

The terms "a" or "an" are used to include one or more than one, and the term "or" is used to refer to a nonexclusive "or" unless otherwise indicated. In addition, it is to be understood that the phraseology or terminology employed herein, and not otherwise defined, is for the purpose of description only and not of limitation. Unless otherwise specified in this disclosure, for construing the scope of the term "about," the error bounds associated with the values (dimensions, operating conditions etc.) disclosed is ±10% of the values indicated in this disclosure. The error bounds associated with the values disclosed as percentages is ±1% of the percentages indicated. The word "substantially" used before a specific word includes the meanings "considerable in extent to that which is specified," and "largely but not wholly that which is specified."

DETAILED DISCLOSURE

Breath aerosol particles contain a variety of nonvolatile organic biomolecules such as metabolites, lipids, and proteins. Further, the nonvolatile molecules have a wide particle size distribution ranging from a sub-micron size to about 10 microns in size. Breath collection and disease diagnostic systems and methods that can efficiently capture different types of nonvolatile molecules of different particle sizes from exhaled breath are required. Particular aspects of the invention are described below in considerable detail for the purpose for illustrating the compositions, and principles, and operations of the disclosed methods and systems. However, various modifications may be made, and the scope of the invention is not limited to the example aspects described.

Figure 2:
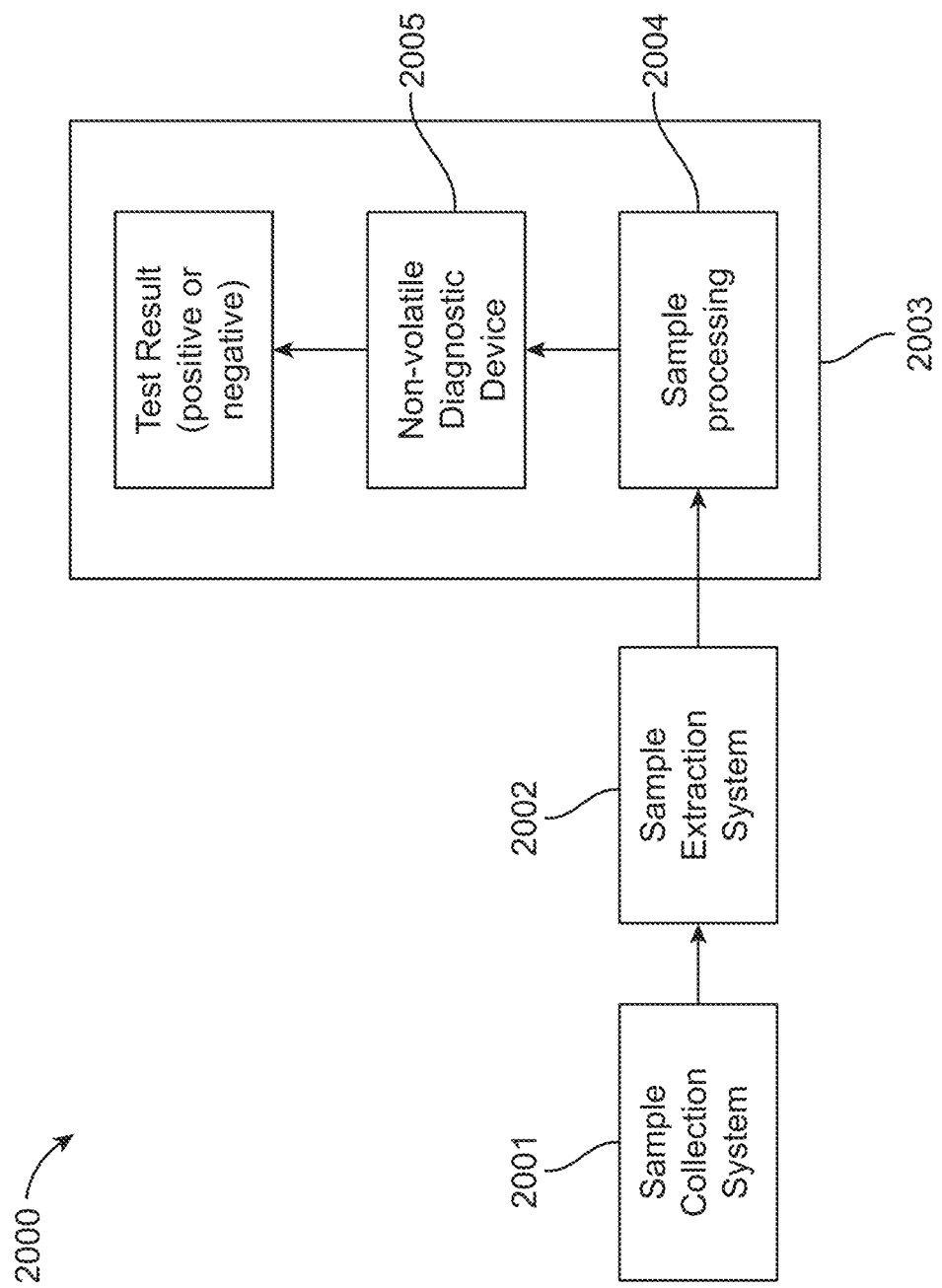
FIG. 2 shows a schematic diagram of an example diagnostic system for respiratory diseases including a sample collection system, according to some implementations.

An example diagnosis system 2000 (FIG. 2) based on exhaled breath analysis ("EBA") may include a breath sample collection system 1000 disposed in fluid communication with a sample extraction system 2002 and an analysis system 2003.

An example exhaled breath sample collection system 1000 (FIG. 1) may include a sample capture element 1001 including a packed bed column to selectively capture breath aerosol including nonvolatile organisms including, but not limited to bacteria and viruses, and molecules including small molecules, lipids, and proteins on very high efficiency adsorbent materials. A trap 1003 is in fluid communication with column 1001 using tubing 1002. Trap 1003 may be made of glass or plastic material. Trap 1003 may be cooled to below ambient temperature using an ice bath or other suitable means. Trap 1003 may be used to collect water vapor, other volatile (check) and nonvolatile molecules that may pass through the collection column as exhaled breath condensate (EBC). During breath analysis of a patient breathing using a ventilator, sample capture element 1001 may be removably connected to the capnography port on the respirator tubing of a ventilator, placing it very near the outlet or at the outlet from the patient's lungs. During breath analysis of a normally breathing person, element 1001 may be removably connected to a mouthpiece (not shown) into which the patient is instructed to breathe or otherwise execute a breath maneuver previously disclosed herein. For example, capture element 1001 may be removably connected downstream (at the outlet) of a breath collection element 1007 (FIG. 1) such as a first aid CPR rescue mask (e.g., as supplied by Dixie USA EMS Supply Co., Model Number EVR-CPR01) worn by the patient during breath analysis. A flow splitter 1008 may be disposed between breath collection element 1007 and capture element 1001 to divide the flow of exhaled breath such that a first portion of exhaled breath is directed to capture element 1001 and a second portion towards a HEPA filter 1009. Flow splitter 1008 may be integrated into collection element 1007. Further, a large particle trap 1012 may be disposed upstream of capture element 1001 to remove large particles of breath condensate (greater than about m) from the exhaled breath stream prior to entering capture element 1001. Pump 1006 may be used to pull exhaled breath into the packed bed column in capture element 1001. An example pump 1006 is a portable diaphragm pump (e.g., Parker Hannifin Corp., Part No.: D737-23-01). The flow rate out of pump 1006 may be adjusted using needle valve 1005 to achieve a desired flow rate. Check valve (one-way flow valve) 1011 may be disposed between pump 1006 and capture element 1001 and is configured to be in an open position only when pump 1006 is pulling exhaled breath through the packed bed column. When there is no flow, valve 1011 is disposed in a closed position. A nominal flow rate of between about 200 ml/min and 600 ml/min may be used. In addition, several capture elements 1001 may be used in parallel to increase the flow rate up to 12 L/min. Further, when one or more capture elements are in collection mode, one or more may be in eluting mode, and the some may be in standby mode. To determine if exhaled breath sample volume was adequate, a $CO_2$ sensor and particle counter (not shown) may be disposed between breath collection element 1007 and sample capture element 1001. $CO_2$ monitoring and particle count allows for an approximation of the proportion of exhaled air volume. A HEPA filter may also be disposed downstream of trap 1003. Capture element 1001 may be cooled using a cooling jacket or other means to reduce the temperature to below ambient temperature to increase the collection efficiency of non-volatile organics particles. The breath sample collection system may further include a humidifier 1010 disposed upstream of the inlet to the capture element to humidify exhaled breath and increase the humidity in the packed bed column.

Breath collection element 1007 may include a tight-fitting mask configured to receive an individual's face and may be removably attached using straps and the like to the face/head of a patient/individual. The individual may sit in an optional containment booth to isolate the patient's EBA from the ambient air in the testing room or area. Element 1007 may be used to collect and direct breath aerosol particles emitted though the mouth and nose of patient into capture element 1001 using pump 1006 as previously described without depositing the aerosol particles on the walls of element 1007. Element 1007 may be disposable to limit the risk of a patient becoming contaminated or infected with a pathogen emitted by a previous patient. Alternatively, element 1007 may be reusable, in which case it may be sterilized.

The example packed bed column in capture element 1001 may include Hamilton PRP-C18 resin beads as supplied by Sigma Aldrich and other vendors. The bed may be held in place between two porous filter plates such as frit discs. For example, a polyethylene disc having an average pore size of above 35 µm may be placed upstream of the bed and a polyethylene disc having an average pore size of 10 µm (Boca Scientific, Dedham, MA) may be placed downstream of the bed. The 35 µm frit disc allows a faster air flow rate while the smaller 10 µm frit disc traps all the C18 resin well. In an example element 1001, the packed bed may include about 25 mg of C18 resin beads having a nominal diameter between about 12 µm and about 20 µm. Non-volatile organic components in exhaled breath removably interact with the C18 functional groups on the beads and are trapped. Water, volatiles and other hydrophilic molecules pass through the bed and may be trapped in glass trap 1003.

Besides C18 functional groups, other functional groups that show affinity to nonvolatile molecules may be used as adsorbents in the column immobilized on solid phase beads such as resin beads. The solid phase beads may be made of polymers and particles such as resins, cellulose, silica, agarose, and hydrated $Fe_3O_4$ nanoparticles. Adsorbent materials may include other functional groups that include, but are not limited to, octadecyl, octyl, ethyl, cyclohexyl, phenyl, cyanopropyl, aminopropyl, 2,3-dihydroxypropoxypropyl, trimethyl-aminopropyl, carboxypropyl, benzenesulfonic acid, and propylsulfonic acid disposed on solid phase beads. Functional groups may also include at least one of ion exchange phases, polymer phases, antibodies, glycans, lipids, DNA and RNA.

Example diagnosis system 2000 (FIG. 2) may include a breath sample collection system 2001 disposed in fluid communication with a sample extraction system 2002 and an analysis system 2003. Sample collection system 2001 may include example sample collection system 1000 (FIG. 1) as previously described. Sample extraction system 2002 may be used to extract the trapped non-volatile organics from the packed bed column in system 1000 and may be disposed in-line or off-line in system 2000. When system 2002 is disposed off-line, at the conclusion of exhaled breath sample collection, capture element 1001 may be removed from system 1000 and eluted with an organic solvent in extraction system 2002 to remove non-volatile organics from the packed bed column. Example organic solvents include, but are not limited to, about 50-70% acetonitrile in water to extract trapped non-volatile organics (strongly polar non-volatile organic molecules, proteins and the like) from the packed bed column. The extraction may be repeated using the same or another solvent, that includes, but is not limited to 50-70% isopropanol in water to extract less polar lipid molecules from the packed bed. Other organic solvents include between about 50% and about 70% methanol in water, and about 50% methanol in about 50% chloroform. When system 2002 is disposed in-line, at least one of a $CO_2$ sensor and particle counter may be disposed upstream of extraction system 2002. System 2002 may include a solvent vessel, a pump to transfer the solvent from the solvent to packed bed column and a vessel to collect the solvent including the non-volatile biomarkers into another vessel or cup. Alternately, system 2002 may include an injector to inject solvent into the packed bed column and collect the extract liquid including non-volatile organics and biomarkers in a suitable cup or vessel, or other laboratory tubes having a small volume. The captured sample in solvent may be further processed and analyzed in analysis system 2003.

Analysis system 2003 may include sample processing system 2004 and at least one diagnostic device 2005. Sample processing system 2004 may include elements necessary to perform one or more of the following steps:

(a) Placing the sample in at least one of a cup, a vial and a sample plate. For example, the Series 110A Spot Sampler (Aerosol Devices) uses 32 well plates with circular well shape (75 µL well volume) or teardrop well shape (120 µL well volume) which are heated to evaporate the solvent and excess fluid/liquid in the sample to concentrate the sample;

(b) Placing the sample in a cup and exposed to a source of vacuum or freeze-drying device to cause the solvent to evaporate to concentrate the sample; and, (c) hot digestion of proteins and virus particles The samples may be centrifuged to remove chemical contamination particles. Many diagnostic devices may be adapted for use in analysis system 2003 that include, but are not limited to devices that perform genomics-based assays (such as PCR, rt-PCR and whole genome sequencing), biomarker recognition assays (such as ELISA), and spectral analysis such as mass spectrometry (MS). Of these diagnostic devices, MS is preferable on account of its speed of analysis. The MS techniques that are preferable for biomarker identification are electrospray ionization (ESI) and matrix assisted laser desorption ionization (MALDI) time of flight MS (TOFMS). ESI may be coupled to high resolution mass spectrometers. MALDI-TOFMS devices may be compact, lightweight, consume less than 100 watts of power and provide sample analysis in less than 15 minutes. MALDI-TOFMS is a preferred diagnostic device for point-of-care diagnostics suitable for ACF. The sample must be dry before it is inserted into the vacuum chamber of the MS and subjected to laser pulses from an ultraviolet laser. This interaction between the sample and the laser creates large, informative biological ion clusters that are characteristic of the biological material. When a concentrated sample is provided by sample processing system 2004 including only trace levels of water or trace levels organic solvents such as 50% to 70% of one of acetonitrile, methanol, and isopropanol in water, sample analysis using MS may take less than 5 minutes (including the sample preparation) because less time is needed to evaporate the water from the sample.

MALDI-TOFMS may be used to identify live/active agents that include, but are not limited to, *B. anthracis* spores (multiple strains), *Y. pestis*, *F. tularensis*, Venezuelan equine encephalitis virus (VEE), Western equine encephalomyelitis virus (WEE), Eastern equine encephalitis virus (EEE), botulinum neurotoxins (BoNT), staphylococcus Enterotoxin (SEA), Staphylococcal enterotoxin B (SEB), ricin, abrin, Ebola Zaire strain, aflatoxins, saxitoxin, conotoxins, Enterobacteria phage T2 (T2), HT-2 toxins (HT2), cobra toxin, biothreat simulants including *B. globigii* spores, *B. cereus* spores, *B. thuringiensis* Al Hakam spores, *B. anthracis* Sterne spores, *Y. enterocolitica*, *E. coli*, MS2 virus, T2 virus, Adenovirus and nonvolatile biochemical threats including NGAs (nonvolatile), bradykinin, oxytocin, Substance P, angiotensin, diazepam, cocaine, heroin, and fentanyl. Further, the example systems and methods disclosed herein may be used to achieve accurate detection and identification of SARS-CoV-2 from human breath samples.

In "matrix assisted laser desorption ionization" (MALDI), the target particle (analyte) is coated by a matrix chemical, which preferentially absorbs light (often ultraviolet wavelengths) from a laser. In the absence of the matrix, the biological molecules would decompose by pyrolysis when exposed to a laser beam in a mass spectrometer. The matrix chemical also transfers charge to the vaporized molecules, creating ions that are then accelerated down a flight tube by the electric field. Microbiology and proteomics have become major application areas for mass spectrometry; examples include the identification of bacteria, discovering chemical structures, and deriving protein functions. MALDI-MS has also been used for lipid profiling of algae. During MALDI-MS, a liquid, usually included an acid, such as trifluoroacetic acid (TFA), and a MALDI matrix chemical such as alpha-cyano-4-hydroxycinnamic acid, is dissolved in a solvent and added to the sample. Solvents include acetonitrile, water, ethanol, and acetone. TFA is normally added to suppress the influence of salt impurities on the mass spectrum of the sample. Water enables hydrophilic proteins to dissolve, and acetonitrile enables the hydrophobic proteins to dissolve. The MALDI matrix solution is spotted on to the sample on a MALDI plate to yield a uniform homogenous layer of MALDI matrix material on the sample. The solvents vaporize, leaving only the recrystallized matrix with the sample spread through the matrix crystals. The acid partially degrades the cell membrane of the sample making the proteins available for ionization and analysis in an MS. Other MALDI matrix materials include 3,5-dimethoxy-4-hydroxycinnamic acid (sinapinic acid), α-cyano-4-hydroxycinnamic acid (α-cyano or α-matrix) and 2,5-dihydroxybenzoic acid (DHB) as described in U.S. Pat. No. 8,409,870.

Further, the volatile organic compounds collected in trap 1003 (FIG. 1) may be warmed using a heater, to drive off the volatile compounds into a diagnostic device such as GC- MS, GC-IMS, volatile ion chromatography, or any other type of analysis method suitable for analyzing volatile organic compounds.

Virus (e.g., SARS-CoV-2) detection is centered on detection of viral proteins, which is a difficult challenge. An example method for virus detection may include a glycan-based capture matrix (beads) to pull the target virus out of the background matrix (e.g., other non-virus biomolecule, contaminants). An aliquot of the sample which may contain a virus, for example, collected using sample collection system 1000, which may also include other background contaminants, may be applied to a bead carrying the capture probe. At least one of glycan, heparin, and carbohydrates may be used as capture materials or probes bound on resin beads or some other types of beads. An optional washing step may be used to remove any nontargeted-virus contaminants. The concentrated and purified virus may be eluted off the beads using suitable solvents into a sealed heating chamber containing an organic acid which may include formic acid or acetic acid and heated to 120° C. for about 10 minutes to digest the proteinaceous toxin down into specific peptide fragments. This hot acid protein digestion protocol cleaves the protein at aspartic acid residues creating a highly reproducible peptide pattern. The capture and digestion processes described may be accomplished with antibodies and enzyme, respectively.

Using this example sample processing for MALDI-TOFMS, sensitivity for ricin biotoxin of better than 100 ng/mL (with S/N of about 50:1) in clean buffer was achieved. At S/N (signal to noise ratio) of 3:1, limits of detection (LOD) of <10 ng/mL may be achieved. For the 1 µL samples used in the MALDI-TOFMS analytical systems, about 10 ng/mL LOD equates to a total mass of about 10 pg ($10^{-12}$ g) on the probe, which is equivalent to about 20,000 viral particles. An example microfluidic sample processing system to implement the method disclosed above may be configured to analyze samples collected from the air or from other sources such as nasal swabs. The glycan-based capture column and other microfluidics components may be reusable. Large fluid reservoirs containing buffer, weak acids, and alcohols may be employed to provide sufficient capacity to measure 100's of samples in one channel of the system. Multiple systems may be run in parallel to process multiple samples simultaneously. Since no fragile and expensive biomolecular reagents are required, the system is cost effective.

Hot acid digestion cleaves the proteins reproducibly at aspartic acid residues creating known peptide sequences with known masses. These peptide mass distributions are characteristic of the progenitor proteins. Thus, digestion provides outstanding specificity if the proteins of interest are largely separated from background materials. Furthermore, the peptide mass distribution is directly determined by the genome, accounting for post-translational modifications. As soon as a new virus is isolated, it is rapidly sequenced. The RNA sequence of the SARS-CoV-2 virus may be used to accurately predict the protein sequences with modern bioinformatics tools (ExPASy bioinformatics portal). These proteins can then be "digested" in silico using bioinformatics tools to create a theoretical peptide map. Thus, the peptides that arise from SARS-COV-2 digestion can be predicted and compared to experimental data to generate a specific MALDI TOFMS signature of the organism. Reports suggest that the predominant proteins in SARS-CoV are characterized by about 46 kDa nucleocapsid protein and the 139 kDa spike proteins. Other proteins in reasonable abundance are E, M and N proteins.

Detection specificity of a target virus will require some level of background removal, particularly if the background contains other proteins. If large amounts of exogenous proteins are present, the peptide map could be dominated by non-target peptides. As previously described, affinity capture probes for the virus toxins based on glycan-decorated agarose beads may be used to readily clean up the toxins, even in large excess of background proteins, and other biomolecules. When analyzing exhaled breath for virus targets such as SARS-CoV-2, other human proteins (FIG. 6 and Example 3) in breath may interfere with detection specificity. An affinity-based cleanup of the sample is required to ensure highest specificity. Virus detection may require bead materials that provide more selective affinity compared to the glycan-decorated beads previously described. For example, dextran-based adsorbents may be used for purifying viruses, including coronaviruses, but the affinity of this resin for the target virus may not be satisfactory. As an alternative, carbohydrates may be used for viral and protein purification including target viruses such as SARS-CoV and SARS-CoV-2. Further heparin, and heparan sulfate may be used as binding agents bound to resin beads. Heparin covalently linked to sepharose beads (GE Healthcare Life Sciences, Heparin Sepharose 6 Fast Flow affinity resin Product #17099801) may be used instead of glycan capture beads. This resin may enable bead-based capture affinity capture system for collecting virus particles from exhaled breath. In an example diagnostic system, exhaled breath samples may be pulled through a capture bed in a sample collection system 1000, collecting particles from the breath. The resin beads (bed) may be washed to remove any background material. The viral particles adsorbed to the beads would then be eluted off using high concentration of acid solution, such as at least one of about 12.5% acetic acid, about 5% TFA, about 5% formic acid and about 10% HCl, into the hot acid digestion chamber to generate the characteristic peptides. The peptide samples may be mixed with MALDI matrix and deposited onto as suitable substrate for MALDI TOFMS analysis. The samples may also be deposited on a suitable substrate or disk that is precoated with MALDI matrix.

Figure 3:
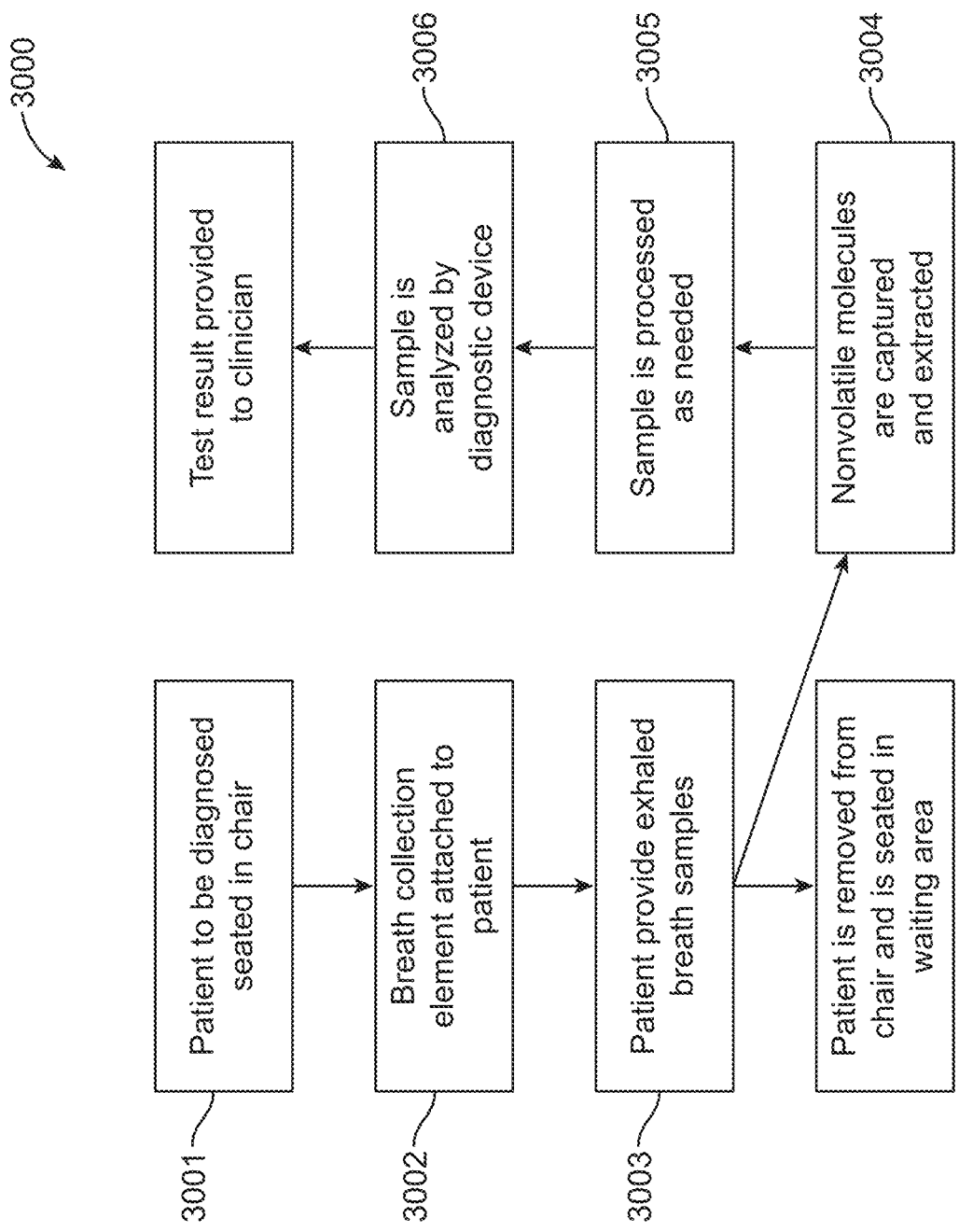
FIG. 3 shows a schematic diagram of an example diagnostic method using a system that includes a packed bed column, according to some implementations.

FIG. 3 is a schematic diagram of an example diagnostic method 3000 using example system 2000. Example method 3000 may be used to perform autonomous point-of-care diagnosis based on exhaled breath. In step 3001, the individual (or patient) may be directed to be seated; the chair may optionally be located in a containment booth. In step 3002, sample breath collection element 1007 may be removably fitted to the individual's head. The individual is then instructed to breathe or perform one or more predetermined maneuvers 3003 which may include a pre-set number of repetitions. Non-volatile organics in breath are captured using system 1000 and extracted using system 2002 in step 3004 and eluted using suitable solvents. During sample collection, human exhaled breath passes through the column at a predetermined flow rate drawn by a pulling pump. Since nonvolatile molecules contained in the exhaled breath interact with the functionalized beads in capture element 1001 (e.g., C18 functional groups immobilized on resin beads), these molecules are trapped in the column bed in element 1001 while hydrophilic molecules including mostly of water and aqueous electrolytes in the breath pass through the column. Nonvolatile organic molecules in human breath show strong affinity for alkyl chains via intermolecular forces including hydrogen bond and noncovalent interaction. The elution of nonvolatile molecules from the column bed may be accomplished using organic solvents that include, but are not limited to, acetonitrile, methanol, and isopropanol as previously described. The sample may be further processed in step 3005 using component 2004. The type of sample processing depends on the type of diagnostic device and the non-volatile analyte particle of interest. As previously described, a virus sample may be subjected to hot acid digestion chamber to generate characteristic peptides. The peptide samples may be mixed with MALDI matrix and deposited onto as suitable substrate for MALDI TOFMS analysis. The samples may also be deposited on a suitable substrate or disk that is precoated with MALDI matrix. The sample is then analyzed by a diagnostic device in step 3006. When the diagnostic device is MALDI-TOFMS, sample processing may also include the steps of plating the sample on to a MALDI-TOFMS sample disk, heating the disk to concentrate the sample, and drying the disk. The sample disk is then analyzed using MALDI-TOFMS. The TOFMS detectors may be modified to incorporate an iron gate and a reflectron to enable analysis and sequencing of COVID-19 type virus peptides that are fragmented during MALDI-TOF/MS. The spectrum obtained is compared to spectra from samples that were known positives to specific respiratory infections, to spectra in known databases, and also to spectra of samples form patients know to be healthy, and a diagnosis of the patient is generated. The result may then be communicated to a clinician or to the patient.

Once the breath collection element 1007 is attached to the patient, and sample extraction is initiated, the example systems and methods may be preferably autonomous (with the exception of asking the patient to the leave the chair after performing the required maneuvers) and generates a test result of the diagnosis. In the case of virus particles like SARS-CoV-2, the particles are about 0.1 micron in diameter and sensitivities may be between about $10^3$ and $10^4$ viral particles.

Reports suggests that analysis of nose and throat swabs from influenza patients and COVID-19 patients produce viral counts of between about $10^3$ and $10^{10}$ viral particles. Less is known about the viral particles count in the breath of patients. Other reports suggest that influenza patients exhaled >$10^4$ particles in about 30 minutes of breathing. If the output of SARS-CoV-2 is similar to that of influenza, an output of $10^3$ to $10^4$ particles in exhaled breath with a particle collection efficiency of >99.9% should be sufficient to identify the target virus particles in exhaled breath using the example methods and systems disclosed herein. Detection time using the example systems and methods may be between about 10 minutes and 20 minutes include the steps of sample extraction (breathing maneuvers), sample collection, sample processing (digestion) and analysis using a MALDI TOF-MS. This detection time is quite rapid compared to existing detection systems.

An example sample processing component may include a hot acid digestion module or cartridge to autonomously extract sample from the packed bed column 1001, perform sample clean-up, conduct the hot acid digestion and provide a sample ready for plating on a MALDI-TOFS sample substrate or disk. The cartridge may be designed for reusability by adding the capability to flush the cartridge between uses.

Figure 7:
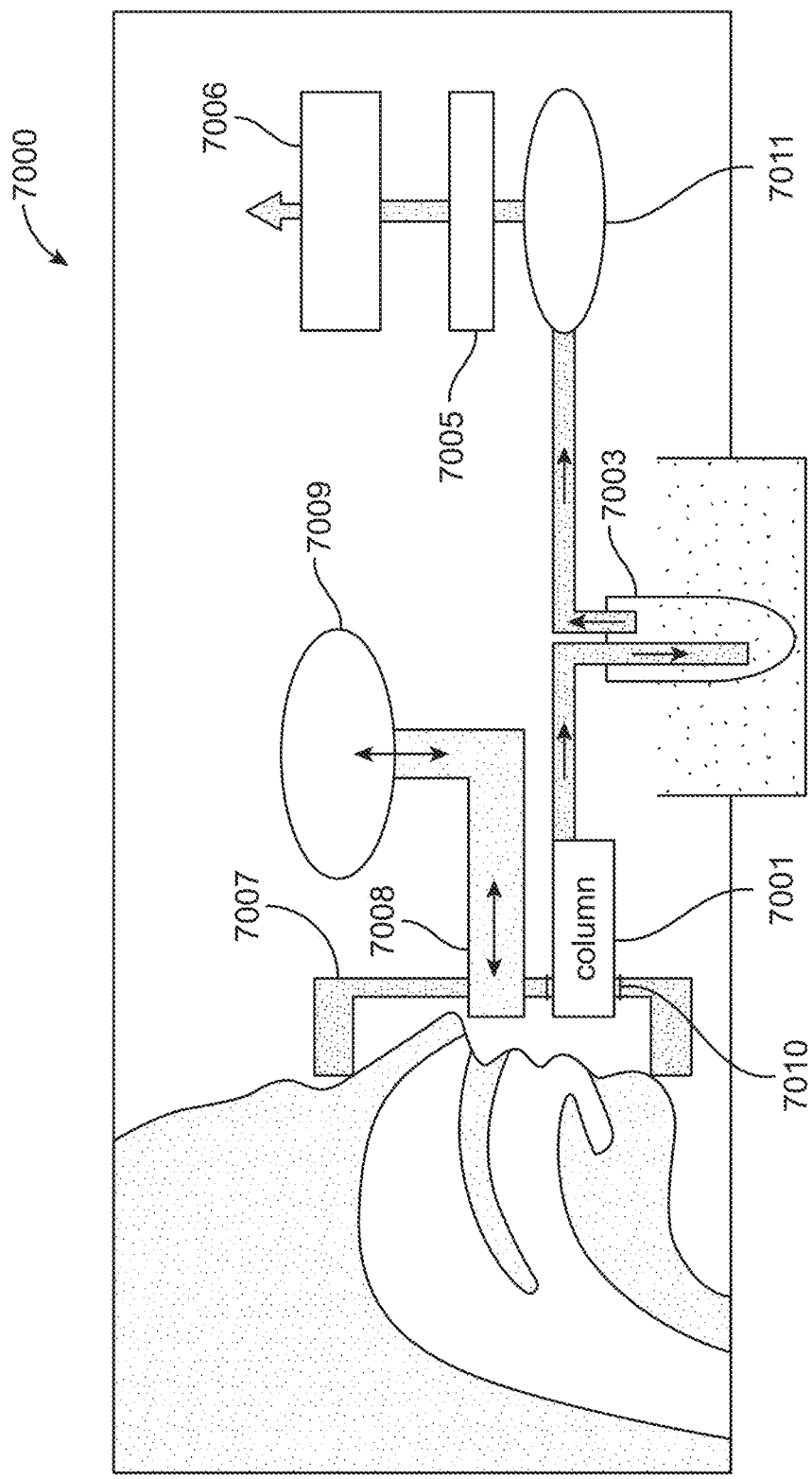
FIG. 7 shows a schematic diagram of an example exhaled breath sample collection system including a packed bed column, according to some implementations.
Figure 8A:
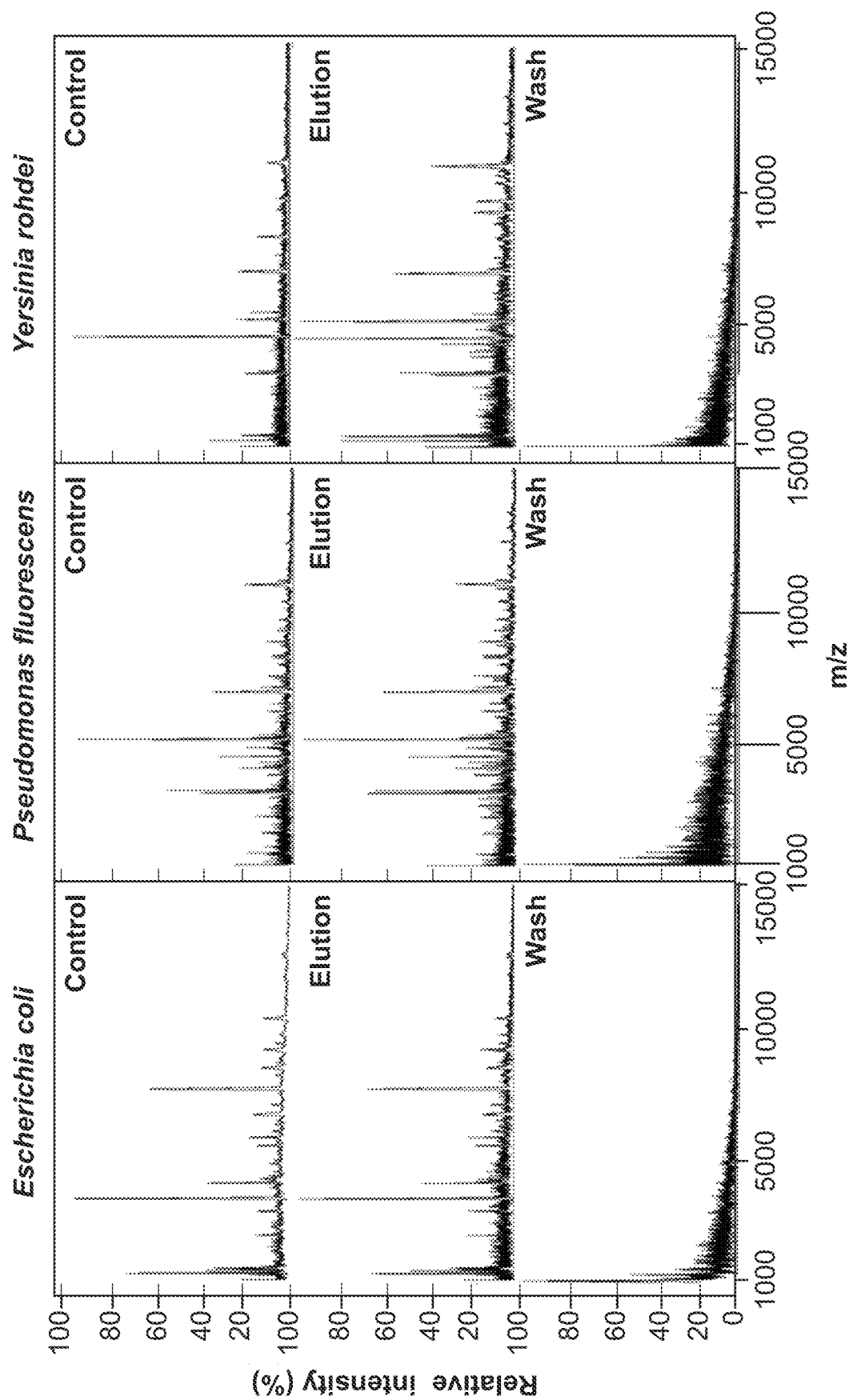
FIGS. 8A and 8B show the results of aerosolized bacteria and virus captured using an example packed bed column and analyzed using MALDI TOF-MS, according to some implementations.
Figure 8B:
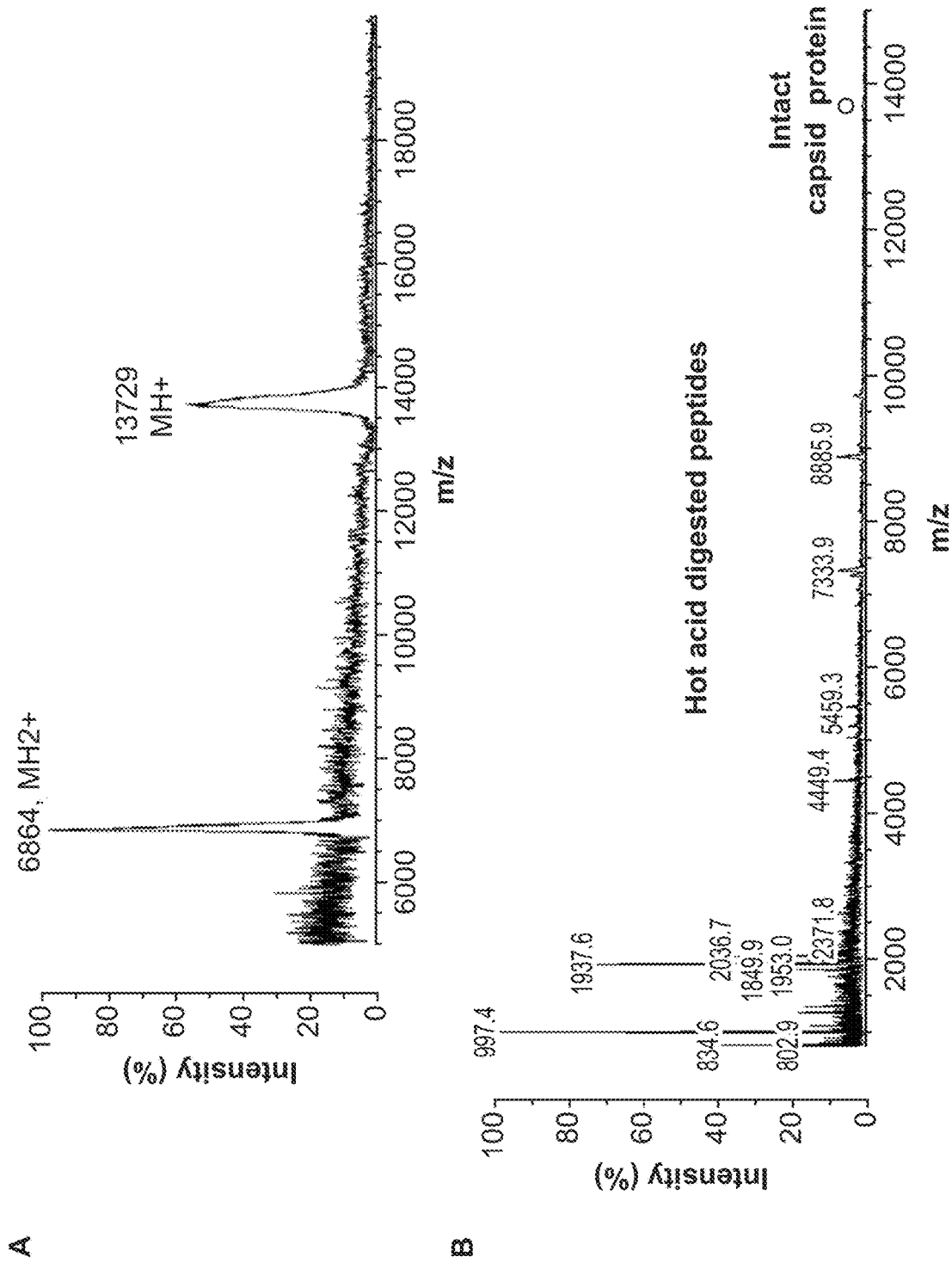

Disclosed in another example sample collection system 7000 (FIG. 7). Example sample capture element 7001 may include a packed bed column including C18-bonded resin beads. These resin beads have C18 functional groups immobilized on the surface. Capture element 7001 may be connected or removably installed to a first aid CPR rescue mask 7007 with minor modifications. The stem 7008 of mask 7007 that usually connects to a resuscitation bag may be modified to removably connect to a HEPA filter 7009. The HEPA filter prevents contamination of exhaled breath by contaminants from ambient air. The oxygen inlet 7010 to the mask is usually located below the stem and configured to be proximate to the chin of a human subject, when a mask is worn by the subject may be modified to removably connect to capture element 7001. Element 7001 may be removably inserted into mask 7007 through inlet 7010 or otherwise removably connected to or inserted into mask 7007 to form a substantially leak-tight fit with mask 7007. Mask 7007 may include elastic bands or ties that may be looped behind the head of a human subject to seal the mask to the face of the patient. Mask 7007 configured as described above prevents direct contact between the mouth and the inlet of the column in element 7001 and minimizes or eliminates contamination of the column inlet by saliva and also maximizes non-volatile organic particle collection from exhaled breath. Trap 7003 immersed in ice water may be installed after (downstream of) capture element 7001. The flow rate (air draw rate) using pump 7006 may be controlled using needle valve 7005 to pull about 600 mL/min. A nominal flow rate of between about 200 ml/min and 600 ml/min may be used. An optional HEPA filter 7011 may be installed between trap 7003 and needle valve 7005. Other fluidic components such as a check valve (see FIG. 1) may be installed in system 7000 to prevent backflow into the column bed in element 7001. $CO_2$ in exhaled breath passes through the column bed in element 7001. To determine if exhaled breath sample volume and/or breathing maneuvers are adequate, a $CO_2$ sensor may be disposed between the outlet of breath capture element 7001 and trap 7003. $CO_2$ monitoring allows for an approximation of the proportion of exhaled air volume. A particle counter may also be installed between the outlet of element 7001 and trap 7003 to detect the size and number for particles exiting the column bed, which may also be used to detect saturation of the bed and breakthrough of nonvolatile organic molecules from the column bed. Example system 7000 may also include a capture element 7001 bypass line (not shown) to enable standardization of breath volume prior to routing into the column bed in element 7001. A C02 sensor and particle counter may also be fluidly connected to the bypass line. The capacity of solid beads immobilized with functional groups in the column bed in capture element 7001 to capture non-volatile organic molecules may be between about 0.05 mg (non-volatile organics)/mg beads and about 0.5 mg/mg. The capacity of C18-bonded resin beads in the column bed in example capture element may be about 0.1 mg/mg. That is, a column bed having 25 mg C18 beads would have the capacity to trap or adsorb about 2.5 mg of non-volatile organic molecules.

Besides C18 functional groups, other functional groups that show affinity to nonvolatile molecules may be used as adsorbents in the column immobilized on solid phase beads such as resin beads. The solid phase beads may be made of polymers and particles such as resins, cellulose, silica, agarose, and hydrated $Fe_3O_4$ nanoparticles. Adsorbent materials may include other functional groups that include, but are not limited to, octadecyl, octyl, ethyl, cyclohexyl, phenyl, cyanopropyl, aminopropyl, 2,3-dihydroxypropoxypropyl, trimethyl-aminopropyl, carboxypropyl, benzenesulfonic acid, and propylsulfonic acid disposed on solid phase beads. Functional groups may also include at least one of ion exchange phases, polymer phases, antibodies, glycans, lipids, DNA and RNA.

The example system and methods described herein are not necessarily limited in their diagnostic capability to respiratory infections. Lung cancer, for example, may also release biomarkers into the peripheral lung fluid, and these biomarkers would be readily detected by the systems and methods disclosed. Furthermore, because blood comes into intimate contact with the alveolar lining in the lungs, biomarkers of infection and cancer in other parts of the body (beyond the lungs) may be transferred across the alveolar lining and into the peripheral lung fluid, and thus, may be detected by the analysis of EBA. As a result, the scope of the invention is not limited to the detection and diagnosis of respiratory disease. The example systems and methods may be used to capture aerosol chemical particles such a ricin and analyze the particles to prevent a chemical attack threat.

EXAMPLES

Example 1. Particle Capture Efficiency Using an Example Packed Bed Column 1001

Figure 4:
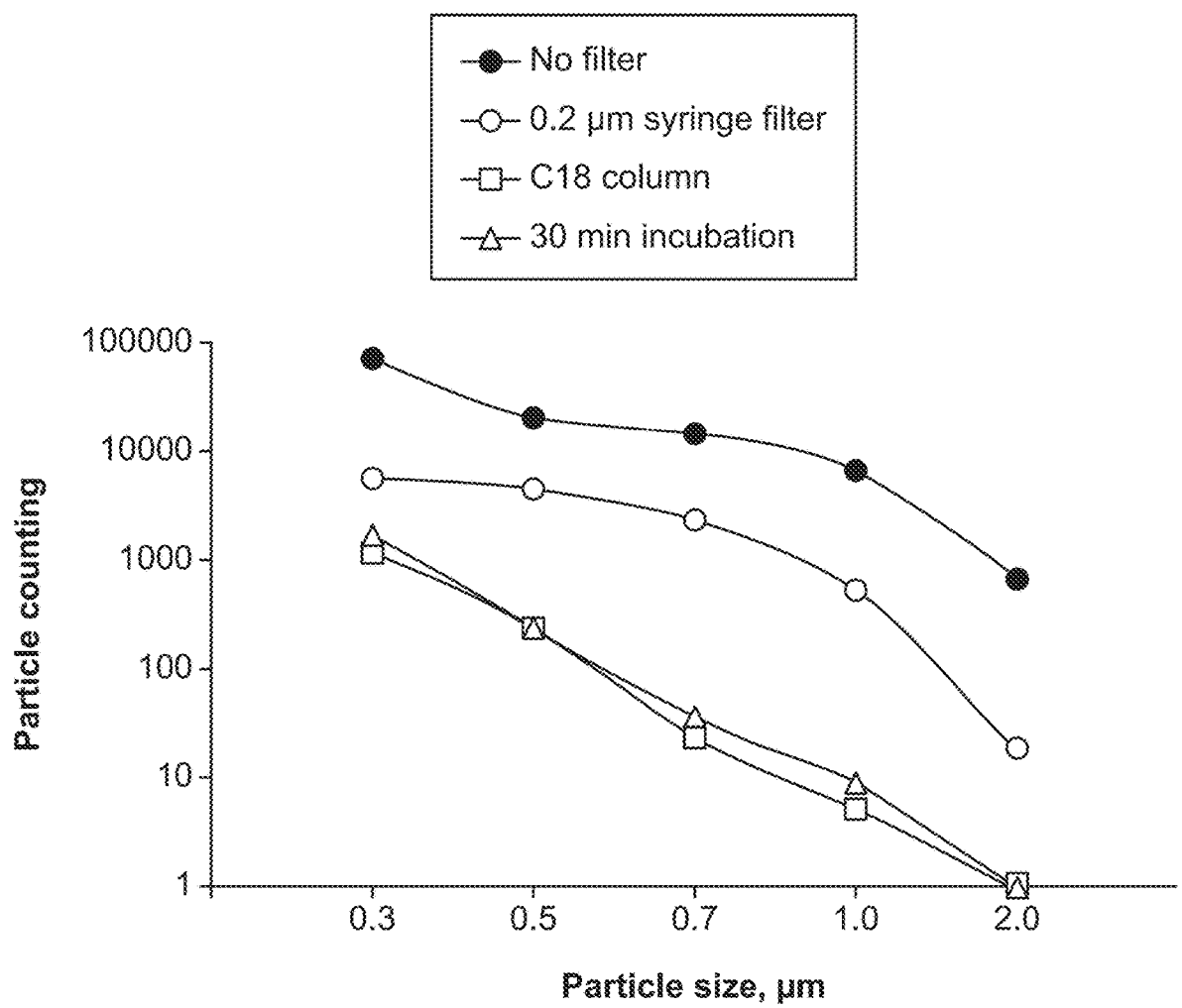
FIG. 4 shows particle capture efficiency measurements using an example packed bed column, according to some implementations.

About 200 µL of HPLC-grade water was aerosolized into a 2-liter chamber using a portable Aeroneb Go nebulizer (Philips, Amsterdam, Netherlands) generating particles of size between about 0.3 µm to 5 µm in size. Column inlet particle size was measured. Particle counts were recorded using a portable laser particle counter (Met One Instruments, Grants Pass, OR) under four test conditions: bare column having no particle bed, column having about 0.2 µm pore-size×25 mm ID syringe filter (VWR International, Radnor, PA), a column 1001 including 30 mg of C18 resin beads (C18 column), and the column 1001 including C18 beads after 30 min. of run time (30 min incubation). The particle counter was located downstream of the column. The particle count for 0.3 µm particles was about 37,000 without the C18-packed column and dropped to about 480 with the C18-packed column (FIG. 4) indicating greater than 99% capture efficiency. A similar capture efficiency was observed for particles of other sizes studied. More importantly, the high capture efficiency was maintained after running the collection for about 30 min. For the 0.3-micron size bin (the most penetrating particle size for filters) the background counts in the laboratory were 146,000 particles/L. When the collection column was attached, the counts dropped to 14 particles/L, which is about a 99.99% collection efficiency (FIG. 4), equivalent or better than a HEPA filter.

Example 2. Analysis of Nonvolatile Organic Molecules Collected Using an Example Packed Bed Column 1001 and MS Based on size and chemical properties, nonvolatile organic molecules may be divided into three broad categories: small polar molecules, small nonpolar molecules (lipids), and macromolecules (peptides and proteins). To demonstrate the collection efficiency of these three types of molecules using example column 1001 including a bed of C18 beads, representative molecules from each category were selected and characterized using high resolution mass spectrometry for the accurate mass measurement. 10 nM methadone (Sigma-Aldrich, St. Louis, MO) was selected to represent small polar molecules, 1,2-Dipalmitoyl-sn-glycero-3-phosphorylcholine (Matreya LLC, State College, PA) to represent lipids, and insulin from porcine pancreas (Sigma-Aldrich) to represent peptides and proteins. About 200 µL of each chemical prepared in HPLC-grade water was aerosolized using a portable Aeroneb Go nebulizer (Philips) into a 50 mL conical tube sitting on a heating block held at about 50° C. Column 1001 including about 30 mg of C18 beads was installed at the bottom of the 50 mL conical tube and the flow rate of pump 1006 was set as about 200 mL/min. The aerosolized chemical in each case was collected for about 5 minutes in the bed in column 1001. After collection of methadone and insulin, the collection column was washed four times with 400 µL of water. After quick centrifugation (which is an optional step), methadone and insulin were eluted using 400 µL of 70% acetonitrile. In the case of phosphorylcholine, the column was washed thrice with about 400 µL of 70% acetonitrile and elution (adsorbate extraction) was accomplished using 400 µL of 70% isopropanol. The washing solutions exiting the bed in each case were saved for analysis. Methadone and insulin collected (extracted) from the bed in column 1001 were lyophilized and re-suspended in 200 µL of 70% acetonitrile with 1% acetic acid. Phosphorylcholine collected from the bed in column 1001 was lyophilized and re-suspended in 200 µL of 50% isopropanol, 25% acetonitrile with 1% acetic acid. Mass spectrometric data of methadone, phosphorylcholine, and insulin were collected using an Orbitrap LTQ mass spectrometer (Thermo Fisher Scientific) via direct infusion in the positive ion mode. The flow rate of direct infusion was set to 3 L/min and the data collection was recorded for 10 min at a resolution of about 60,000 at 200 m/z. Target molecules were identified by accurate mass measurement. As shown in FIG. 5, mass spectrometric signals for each representative molecule were only detected in the elution solution including molecules extracted from the C18 bed, but not in the washing solution. Example column 1001 with a bed of C18 beads is therefore effective in collecting small polar molecules, small nonpolar molecules (lipids), and macromolecules (peptides and proteins) and is capable of high efficiency sample collection of these types of nonvolatile organic molecules.

Example 3. Analysis of Exhaled Breath Collected from Human Subjects

In example system 7000 previously described, the column in element 7001 included about 25 mg of C18 beads. Breath samples were collected from four healthy human subjects having different breathing volumes with the same flow rate: subject 1 producing 144 L breathing volume, subject 2 producing 40 L, subject 3 and subject 4 producing 81 L. After breath sample collection, the collection column was removed and eluted with 400 µL of 70% acetonitrile for the collection of small polar molecules and proteins. The protein samples were lyophilized to remove the solvent and resuspended in 100 µL of 0.1% formic acid. Then, the column was eluted with 400 µL of 70% isopropanol for the collection of nonpolar molecules (lipids).

Samples were analyzed using SDS-PAGE electrophoresis and bottom-up proteomics. Electrophoresis was conducted using a Criterion Tris-HCl Gel system (Bio-Rad Laboratories, Hercules, CA) and using about 25 µL of the collected sample corresponding to each subject. After SDS-PAGE electrophoresis, the SDS-PAGE gel was treated with silver staining (Thermo Fisher Scientific) for the visualization of proteins. Bovine serum albumin (BSA) was used an internal positive control. During bottom-up proteomics, about 50 µL of total collected sample corresponding to each subject was treated as described herein. Briefly, about 50 µL of 50 mM ammonia bicarbonate (pH 8.5) was added to each sample. Protein reduction was conducted by adding dithiothreitol to the final concentration of 5 mM and incubated for 30 min at 37° C. After reduction, protein alkylation was followed by adding iodoacetamide to the final concentration of 15 mM and incubated for 1 h at room temperature. Trypsin (Thermo Fisher Scientific) was used for overnight protein digestion. After digestion, peptides were cleaned using C18-packed tips (Glygen, Columbia, MD). Final peptide samples were constructed in 20 µL of 0.1% formic acid for mass spectrometry analysis. The samples were processed using an EASY-nLC 1000 system (Thermo Fisher Scientific) coupled to a Q Exactive HF Hybrid Quadrupole-Orbitrap mass spectrometer (Thermo Fisher Scientific). During tandem mass spectrometry analysis, peptides were loaded into an Acclaim PepMap 100 C18 trap column (0.2 mm×20 mm, Thermo Fisher Scientific) with a flow rate of 5 µl/min and separated on an EASY-Spray HPLC Column (75 m×150 mm, Thermo Fisher Scientific). HPLC gradient was conducted using 5-55% of the mobile phase (75% acetonitrile and 0.1% formic acid) with a flow rate of 300 nL/min for 60 minutes. Mass spectrometry data collection was conducted in the data-dependent acquisition mode. Precursor scanning resolution was set to 60,000 and product ion scanning resolution to 15,000. Product ion fragmentation was accomplished using high energy collision-induced disassociation (HCD) with about 27% of total energy. Bottom-up proteomics raw data files were processed with MaxQuant-Andromeda software against the UniProt human protein database/knowledgebase.

Figure 6A:
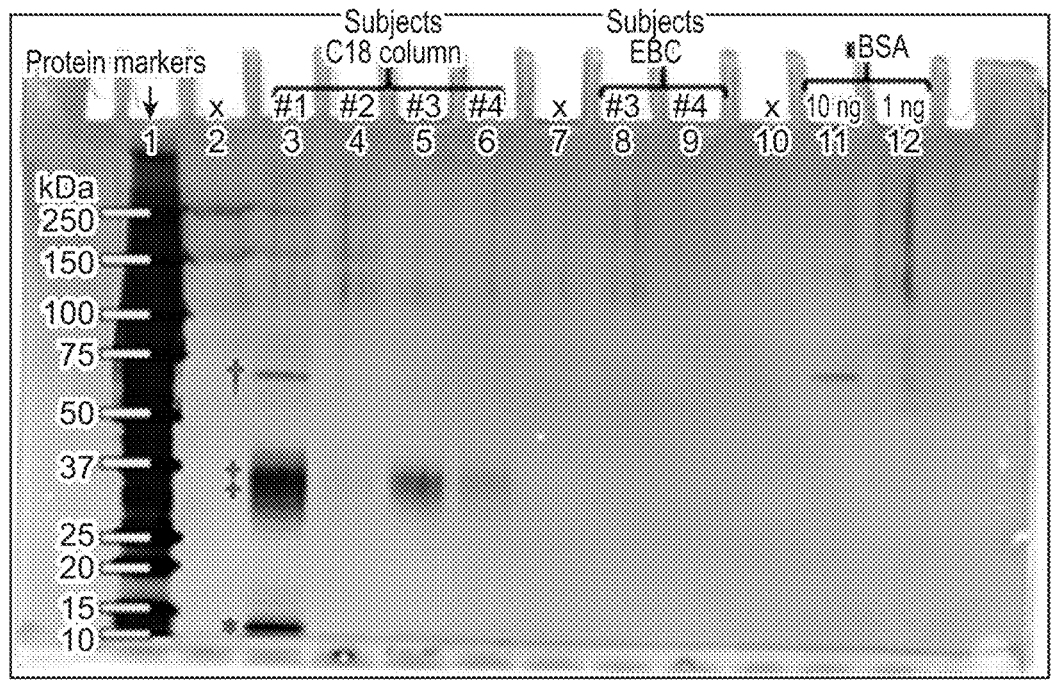
FIGS. 6A and 6B depict silver staining images with SDS-PAGE electrophoresis of proteins in exhaled breath samples, and spectra collected using total ion chromatography (TIC) in LC-MS analysis of exhaled breath samples, respectively, according to some implementations.
Figure 6B:
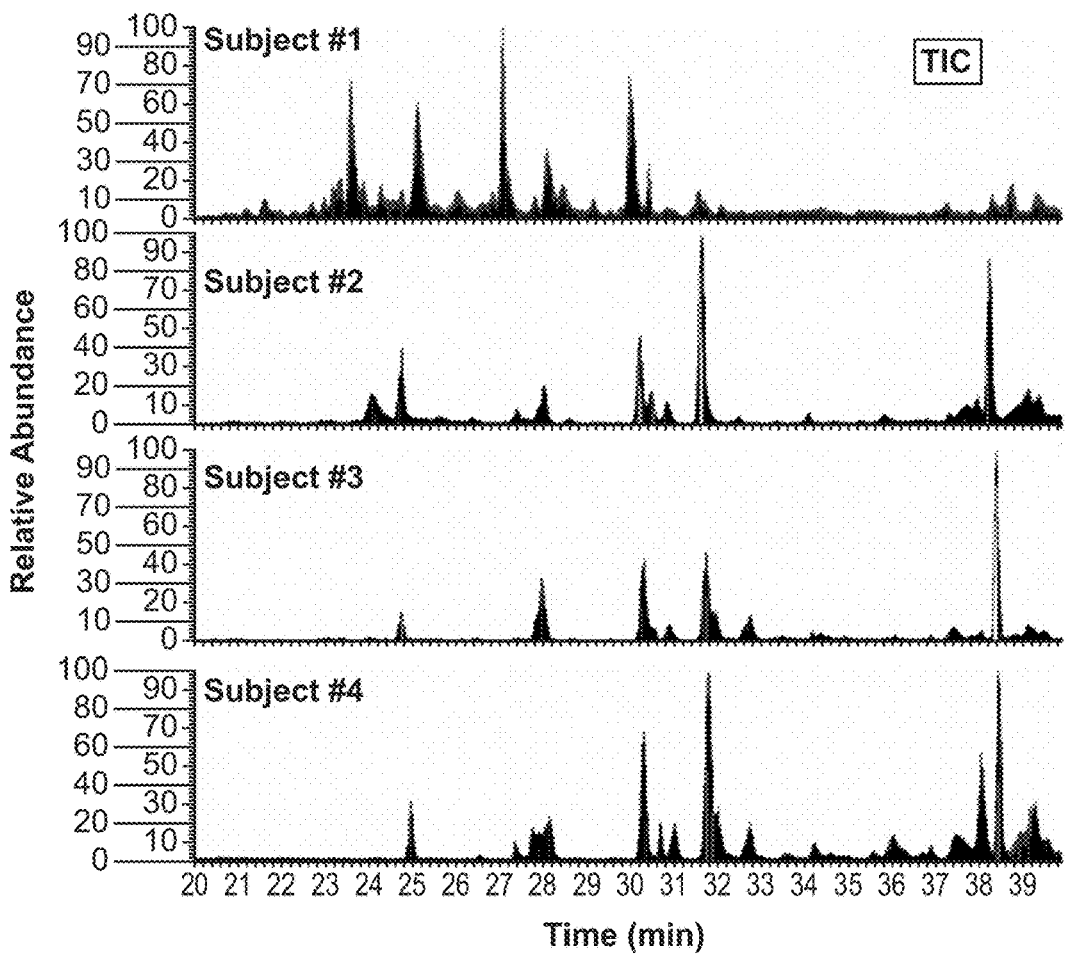

FIG. 6A shows gel electrophoresis silver staining images for the four subjects. "X" denotes the lane contained no sample and was used as an internal negative control. Protein bands were not observed in the condensate (EBC) samples collected in trap 7003. The darkness intensity of the protein bands suggests the protein content in all the samples was greater than 10 ng per protein band, which is adequate for sequential bottom-up proteomics. In addition, a similar protein band pattern for the human subjects may be observed as the most intense protein bands appear at between about 50 kDa and about 75 kDa (band #1), at about 37 kDa (band #2), and between about 10 kDa and about 15 kDa (band #3). By using tandem mass spectrometry, proteins corresponding to band #1 were identified as serum albumin and keratins, proteins corresponding to band #2 as zinc-alpha-2-glycoprotein, and proteins corresponding to band #3 as cystatin, dermcidin, and S100 proteins. In addition, the protein clusters at about 37 kDa (band #2) suggests that protein post-translational modifications, presumably glycosylation, may occur. Bottom-up proteomics and protein database searching confirmed that this protein is zinc-alpha-2-glycoprotein, a protein with four known N-linked glycosylation sites (UniProt knowledgebase). The results indicate that silver staining-based protein visualization coupled with bottom-up proteomics may be used to identify protein profiles in exhaled breath samples even with very low protein concentration. Further, the intensity of the protein bands may be correlated with the collected breath volume as subject 1, who producing about 144 liters of exhaled breath, showed the darkest protein bands and subject 2 (40 liters) showed the lightest bands. Differences in breathing manners or protocols may also affect aerosol particle product production from each subject, which could contribute to uneven protein distribution in different subjects. No specific instruction on the breathing manner was used in the above exercise. The similar protein pattern was further confirmed in the TIC profile using tandem mass spectrometry (FIG. 6B). By using different protein analysis techniques, the results strongly indicated that the column collection system was able to capture proteins from exhaled breath and the protein content in the breath samples encouraged the sequential protein identification using bottom-up proteomics. In addition, major proteins in saliva, such as alpha amylase, were not identified suggesting that the modifications to example facial mask 7007 prevented direct contact with the subject's mouth and the capture element 7001. The example breath collection system disclosed herein may be used to effectively capture proteins from the lower respiratory airways.

The similarity in protein patterns in exhaled breath collected from the four subjects was further confirmed by total ion chromatography (TIC) in LC-MS analysis as shown in FIG. 6B. Ion chromatography peak patterns were similar for the four subjects and subject 1 showed relatively more intense peaks similar to the more intense bands seen in the staining images in FIG. 6A.

Bottom-up proteomics was used for the identification of proteins in the collected exhaled breath samples. 197 proteins were identified from subject 1, 47 proteins from subject 2, 25 proteins from subject 3, and 64 proteins for subject 4. The protein identification numbers are consistent with the protein content in the samples as subject 1 had the most proteins identified. In total, 303 proteins were identified from the 4 subjects. The most abundant proteins identified based on spectral matching are listed in Table 1, and include cystatin-A, dermcidin, and several members in the S100 protein family.

TABLE 1

The top 20 proteins identified from the breath samples from the four subjects based on the abundance.

| Accession ID | Protein Identification | Sequence coverage [%] | Mol. weight [kDa] | Sequence length (aa) | MS/MS count |
| --- | --- | --- | --- | --- | --- |
| P01040 | Cystatin-A OS = Homo sapiens OX = 9606 GN = CSTA PE = 1 SV = 1 | 100 | 11 | 98 | 46 |
| P81605 | Dermcidin OS = Homo sapiens OX = 9606 GN = DCD PE = 1 SV = 2 | 43.6 | 11 | 110 | 35 |
| P31151 | Protein S100-A7 OS = Homo sapiens OX = 9606 GN = S100A7 | 88.1 | 11 | 101 | 28 |
| Q9NZT1 | Calmodulin-like protein 5 OS = Homo sapiens OX = 9606 | 95.9 | 16 | 146 | 26 |
| P62987 | Ubiquitin-60S ribosomal protein L40 OS = Homo sapiens OX = 9606 GN = UBA52 PE = 1 SV = 2; sp | 57.8 | 15 | 128 | 23 |
| P00441 | Superoxide dismutase [Cu—Zn] OS = Homo sapiens OX = 9606 | 99.4 | 16 | 154 | 17 |

TABLE 1-continued

The top 20 proteins identified from the breath samples from the four subjects based on the abundance.

| Accession ID | Protein Identification | Sequence coverage [%] | Mol. weight [kDa] | Sequence length (aa) | MS/MS count |
|---|---|---|---|---|---|
| P25311 | Zinc-alpha-2-glycoprotein OS = Homo sapiens OX = 9606 | 41.6 | 34 | 298 | 12 |
| P31944 | Caspase-14 OS = Homo sapiens OX = 9606 GN = CASP14 PE = 1 | 38.8 | 28 | 242 | 11 |
| P01036 | Cystatin-S OS = Homo sapiens OX = 9606 GN = CST4 PE = 1 SV = 3 | 59.6 | 16 | 141 | 11 |
| P02768 | Serum albumin OS = Homo sapiens OX = 9606 GN = ALB PE = 1 | 14.6 | 69 | 609 | 10 |
| P0DP25 | Calmodulin-3 OS = Homo sapiens OX = 9606 GN = CALM3 PE = 1 | 38.3 | 17 | 149 | 9 |
| P04264 | Keratin, type II cytoskeletal 1 OS = Homo sapiens OX = 9606 | 18.3 | 66 | 644 | 9 |
| Q6UWP8 | Suprabasin OS = Homo sapiens OX = 9606 GN = SBSN PE = 1 SV = 2 | 20.7 | 61 | 590 | 9 |
| P02538 | Keratin, type II cytoskeletal 6A OS = Homo sapiens OX = 9606 | 15.1 | 60 | 564 | 7 |
| P13645 | Keratin, type I cytoskeletal 10 OS = Homo sapiens OX = 9606 | 7.4 | 59 | 584 | 6 |
| P31025 | Lipocalin-1 OS = Homo sapiens OX = 9606 GN = LCN1 PE = 1 | 19.3 | 19 | 176 | 5 |
| O14529 | Homeobox protein cut-like 2 OS = Homo sapiens OX = 9606 | 1.9 | 162 | 1486 | 4 |
| Q6E0U4 | Dermokine OS = Homo sapiens OX = 9606 GN = DMKN PE = 1 | 10.5 | 47 | 476 | 4 |
| Q08554 | Desmocollin-1 OS = Homo sapiens OX = 9606 GN = DSC1 PE = 1 | 5 | 100 | 894 | 4 |
| Q02413 | Desmoglein-1 OS = Homo sapiens OX = 9606 GN = DSG1 PE = 1 | 6 | 114 | 1049 | 4 |

Nonvolatile organic molecules contained in exhaled air could originate from both upper and lower respiratory airways. To reveal the tissue origin of the proteins identified in the study described above, the identified proteins were compared with five published proteome databases from bronchoalveolar lavage fluid (BALF). It is well known that BALF breath sampling methods produce proteins from the origin of lower respiratory airways. The comparison showed that about 63 proteins identified in the above-described study (Table 2) was reported in BALF proteomics databases, suggesting that the example breath sample collection system and method disclosed herein was effective in capturing proteins that originate from the lower respiratory airways such as lung tissues. No proteins were identified that correlated with either bacteria or viruses suggesting that the volunteers were indeed healthy. Therefore, the example methods and systems disclosed herein may be used as a diagnostic tool for detection of respiratory diseases based on identification of proteins in exhaled breath.

TABLE 2

Proteins corresponding to the breath samples from the four subjects.

| Accession | Protein Identification | Sequence coverage [%] | Mol. weight [kDa] | Sequence length (aa) | MS/MS count |
|---|---|---|---|---|---|
| P01040 | HUMAN Cystatin-A OS = Homo sapiens OX = 9606 GN = CSTA PE = 1 SV = 1 | 100 | 11 | 98 | 46 |
| P00441 | HUMAN Superoxide dismutase [Cu—Zn] OS = Homo sapiens OX = 9606 GN = SOD1 PE = 1 SV = 2 | 99.4 | 16 | 154 | 17 |
| P25311 | HUMAN Zinc-alpha-2-glycoprotein OS = Homo sapiens OX = 9606 GN = AZGP1 PE = 1 SV = 2 | 41.6 | 34 | 298 | 12 |
| P01036 | HUMAN Cystatin-S OS = Homo sapiens OX = 9606 GN = CST4 PE = 1 SV = 3 | 59.6 | 16 | 141 | 11 |
| P02768 | HUMAN Serum albumin OS = Homo sapiens OX = 9606 GN = ALB PE = 1 SV = 2 | 14.6 | 69 | 609 | 10 |
| P04264 | HUMAN Keratin, type II cytoskeletal 1 OS = Homo sapiens OX = 9606 GN = KRT1 PE = 1 SV = 6; | 18.3 | 66 | 644 | 9 |
| P13645 | HUMAN Keratin, type I cytoskeletal 10 OS = Homo sapiens OX = 9606 GN = KRT10 PE = 1 SV = 6; | 7.4 | 59 | 584 | 6 |
| P31025 | HUMAN Lipocalin-1 OS = Homo sapiens OX = 9606 GN = LCN1 PE = 1 SV = 1; sp | 19.3 | 19 | 176 | 5 |
| Q01469 | HUMAN Fatty acid-binding protein 5 OS = Homo sapiens OX = 9606 GN = FABP5 PE = 1 SV = 3 | 23.7 | 15 | 135 | 4 |
| Q04695 | HUMAN Keratin, type I cytoskeletal 17 OS = Homo sapiens OX = 9606 GN = KRT17 PE = 1 SV = 2; | 11.1 | 48 | 432 | 4 |
| P06702 | HUMAN Protein S100-A9 OS = Homo sapiens OX = 9606 GN = S100A9 PE = 1 SV = 1 | 28.9 | 13 | 114 | 4 |

TABLE 2-continued

Proteins corresponding to the breath samples from the four subjects.

| Accession | Protein Identification | Sequence coverage [%] | Mol. weight [kDa] | Sequence length (aa) | MS/MS count |
|---|---|---|---|---|---|
| P29508 | HUMAN Serpin B3 OS = Homo sapiens OX = 9606 GN = SERPINB3 PE = 1 SV = 2 | 13.1 | 45 | 390 | 4 |
| P10599 | HUMAN Thioredoxin OS = Homo sapiens OX = 9606 GN = TXN PE = 1 SV = 3 | 50.5 | 12 | 105 | 4 |
| P04040 | HUMAN Catalase OS = Homo sapiens OX = 9606 GN = CAT PE = 1 SV = 3 | 9.1 | 60 | 527 | 3 |
| P01037 | HUMAN Cystatin-SN OS = Homo sapiens OX = 9606 GN = CST1 PE = 1 SV = 3 | 33.3 | 16 | 141 | 3 |
| P04406 | HUMAN Glyceraldehyde-3-phosphate dehydrogenase OS = Homo sapiens OX = 9606 GN = GAPDH PE = 1 SV = 3 | 15.2 | 36 | 335 | 3 |
| P12273 | HUMAN Prolactin-inducible protein OS = Homo sapiens OX = 9606 GN = PIP PE = 1 SV = 1 | 19.9 | 17 | 146 | 3 |
| P04075 | HUMAN Fructose-bisphosphate aldolase A OS = Homo sapiens OX = 9606 GN = ALDOA PE = 1 SV = 2 | 10.7 | 39 | 364 | 2 |
| P07355 | HUMAN Annexin A2 OS = Homo sapiens OX = 9606 GN = ANXA2 PE = 1 SV = 2; sp | 6.8 | 39 | 339 | 2 |
| P01833 | HUMAN Polymeric immunoglobulin receptor OS = Homo sapiens OX = 9606 GN = PIGR PE = 1 SV = 4 | 3.4 | 83 | 764 | 2 |
| Q06830 | HUMAN Peroxiredoxin-1 OS = Homo sapiens OX = 9606 GN = PRDX1 PE = 1 SV = 1 | 13.1 | 22 | 199 | 2 |
| P32119 | HUMAN Peroxiredoxin-2 OS = Homo sapiens OX = 9606 GN = PRDX2 PE = 1 SV = 5 | 16.7 | 22 | 198 | 2 |
| P63104 | HUMAN 14-3-3 protein zeta/delta OS = Homo sapiens OX = 9606 GN = YWHAZ PE = 1 SV = 1 | 5.7 | 28 | 245 | 1 |
| P01011 | HUMAN Alpha-1-antichymotrypsin OS = Homo sapiens OX = 9606 GN = SERPINA3 PE = 1 SV = 2 | 7.1 | 48 | 423 | 1 |
| P17174 | HUMAN Aspartate aminotransferase, cytoplasmic OS = Homo sapiens OX = 9606 GN = GOT1 PE = 1 SV = 3 | 3.4 | 46 | 413 | 1 |
| P30838 | HUMAN Aldehyde dehydrogenase, dimeric NADP-preferring OS = Homo sapiens OX = 9606 GN = ALDH3A1 SV = 3 | 2.6 | 50 | 453 | 1 |
| P04083 | HUMAN Annexin A1 OS = Homo sapiens OX = 9606 GN = ANXA1 PE = 1 SV = 2 | 4.6 | 39 | 346 | 1 |
| P05089 | HUMAN Arginase-1 OS = Homo sapiens OX = 9606 GN = ARG1 PE = 1 SV = 2 | 4.7 | 35 | 322 | 1 |
| Q13867 | HUMAN Bleomycin hydrolase OS = Homo sapiens OX = 9606 GN = BLMH PE = 1 SV = 1 | 3.5 | 53 | 455 | 1 |
| P13987 | HUMAN CD59 glycoprotein OS = Homo sapiens OX = 9606 GN = CD59 PE = 1 SV = 1 | 8.6 | 14 | 128 | 1 |
| P23528 | HUMAN Cofilin-1 OS = Homo sapiens OX = 9606 GN = CFL1 PE = 1 SV = 3 | 7.2 | 19 | 166 | 1 |
| P54108 | HUMAN Cysteine-rich secretory protein 3 OS = Homo sapiens OX = 9606 GN = CRISP3 PE = 1 SV = 1 | 5.7 | 28 | 245 | 1 |
| P04080 | HUMAN Cystatin-B OS = Homo sapiens OX = 9606 GN = CSTB PE = 1 SV = 2 | 24.5 | 11 | 98 | 1 |
| P28325 | HUMAN Cystatin-D OS = Homo sapiens OX = 9606 GN = CST5 PE = 1 SV = 1 | 9.9 | 16 | 142 | 1 |
| Q15828 | HUMAN Cystatin-M OS = Homo sapiens OX = 9606 GN = CST6 PE = 1 SV = 1 | 7.4 | 17 | 149 | 1 |
| P09228 | HUMAN Cystatin-SA OS = Homo sapiens OX = 9606 GN = CST2 PE = 1 SV = 1 | 23.4 | 16 | 141 | 1 |
| Q8TDM6 | HUMAN Disks large homolog 5 OS = Homo sapiens OX = 9606 GN = DLG5 PE = 1 SV = 4 | 1 | 214 | 1919 | 1 |
| P78417 | HUMAN Glutathione S-transferase omega-1 OS = Homo sapiens OX = 9606 GN = GSTO1 PE = 1 SV = 2 | 7.5 | 28 | 241 | 1 |
| P04792 | HUMAN Heat shock protein beta-1 OS = Homo sapiens OX = 9606 GN = HSPB1 PE = 1 SV = 2 | 11.7 | 23 | 205 | 1 |
| P35527 | HUMAN Keratin, type I cytoskeletal 9 OS = Homo sapiens OX = 9606 GN = KRT9 PE = 1 SV = 3; | 3.4 | 62 | 623 | 1 |
| P35908 | HUMAN Keratin, type II cytoskeletal 2 epidermal OS = Homo sapiens OX = 9606 GN = KRT2 PE = 1 SV = 2;; | 3.9 | 65 | 639 | 1 |
| P30086 | HUMAN Phosphatidylethanolamine-binding protein 1 OS = Homo sapiens OX = 9606 GN = PEBP1 PE = 1 SV-3 | 8 | 21 | 187 | 1 |
| P30041 | HUMAN Peroxiredoxin-6 OS = Homo sapiens OX = 9606 GN = PRDX6 PE = 1 SV = 3 | 10.3 | 25 | 224 | 1 |
| P25789 | HUMAN Proteasome subunit alpha type-4 OS = Homo sapiens OX = 9606 GN = PSMA4 PE = 1 SV = 1 | 3.4 | 29 | 261 | 1 |
| P06454 | HUMAN Prothymosin alpha OS = Homo sapiens OX = 9606 GN = PTMA PE = 1 SV = 2 | 15.3 | 12 | 111 | 1 |
| O00391 | HUMAN Sulfhydryl oxidase 1 OS = Homo sapiens OX = 9606 GN = QSOX1 PE = 1 SV = 3 | 1.5 | 83 | 747 | 1 |

TABLE 2-continued

Proteins corresponding to the breath samples from the four subjects.

| Accession | Protein Identification | Sequence coverage [%] | Mol. weight [kDa] | Sequence length (aa) | MS/MS count |
|---|---|---|---|---|---|
| Q8NFJ5 | HUMAN Retinoic acid-induced protein 3 OS = Homo sapiens OX = 9606 GN = GPRC5A PE = 1 SV = 2 | 3.9 | 40 | 357 | 1 |
| P31949 | HUMAN Protein S100-A11 OS = Homo sapiens OX = 9606 GN = S100A11 PE = 1 SV = 2 | 10.5 | 12 | 105 | 1 |
| P60174 | HUMAN Triosephosphate isomerase OS = Homo sapiens OX = 9606 GN = TPI1 PE = 1 SV = 3 | 3.8 | 31 | 286 | 1 |
| P35030 | HUMAN Trypsin-3 OS = Homo sapiens OX = 9606 GN = PRSS3 PE = 1 SV = 2 | 4.3 | 33 | 304 | 1 |
| Q13404 | HUMAN Ubiquitin-conjugating enzyme E2 variant 1 OS = Homo sapiens OX = 9606 GN = UBE2V1 PE = 1 SV = 2 | 8.2 | 16 | 147 | 1 |
| P14618 | HUMAN Pyruvate kinase PKM OS = Homo sapiens OX = 9606 GN = PKM PE = 1 SV = 4; sp | 2.1 | 58 | 531 | 1 |
| O95613 | HUMAN Pericentrin OS = Homo sapiens OX = 9606 GN = PCNT PE = 1 SV = 4 | 0.3 | 378 | 3336 | 1 |
| Q96FV2 | HUMAN Secernin-2 OS = Homo sapiens OX = 9606 GN = SCRN2 PE = 1 SV = 3 | 7.3 | 47 | 425 | 1 |
| Q07955 | HUMAN Serine/arginine-rich splicing factor 1 OS = Homo sapiens OX = 9606 GN = SRSF1 PE = 1 SV = 2 | 12.1 | 28 | 248 | 1 |
| O14979 | HUMAN Heterogeneous nuclear ribonucleoprotein D-like OS = Homo sapiens OX = 9606 GN = HNRNPDL PE = 1 SV = 3 | 1 | 6 | 6 | 1 |
| P08727 | HUMAN Keratin, type I cytoskeletal 19 OS = Homo sapiens OX = 9606 GN = KRT19 PE = 1 SV = 4;;; sp | 1 | 2 | 1.8 | 1 |
| Q14152 | HUMAN Eukaryotic translation initiation factor 3 subunit A OS = Homo sapiens OX = 9606 GN = EIF3A PE = 1 SV = 1 | 1.3 | 167 | 1382 | 1 |
| P15586 | HUMAN N-acetylglucosamine-6-sulfatase OS = Homo sapiens OX = 9606 GN = GNS PE = 1 SV = 3 | 2.4 | 62 | 552 | 1 |
| Q96T58 | HUMAN Msx2-interacting protein OS = Homo sapiens OX = 9606 GN = SPEN PE = 1 SV = 1 | 1 | 1 | 0.6 | 1 |
| P00734 | HUMAN Prothrombin OS = Homo sapiens OX = 9606 GN = F2 PE = 1 SV = 2 | 1 | 3 | 3.1 | 1 |
| Q687X5 | HUMAN Metalloreductase STEAP4 OS = Homo sapiens OX = 9606 GN = STEAP4 PE = 1 SV = 1 | 1 | 4 | 4.1 | 1 |
| P23470 | HUMAN Receptor-type tyrosine-protein phosphatase gamma OS = Homo sapiens OX = 9606 GN = PTPRG PE = 1 SV = 4 | 1 | 0 | 0 | 1 |

Example 4. Capture and Analysis of Aerosolized Bacteria and Virus Using an Example Packed Bed Column 1001 and MALDI TOF-MS One virus sample, Bacteriophage MS2, and three bacteria, Escherichia coli (E. coli*), *Pseudomonas fluorescens*, and *Yersinia rohdei* were acquired from American Type Culture Collection (ATCC, Manassas, VA). 5 μL of each sample was prepared in 200 μL of HPLC-grade water and aerosolized using a portable Aeroneb Go nebulizer (Philips) into a 50 mL tube. The collection column which includes 25 g to 35 g of C18 beads was fluidly connected near the bottom of the 50 mL tube and a pump was used to draw the nebulized sample into and through the column. The flow rate of the pump was set at about 200 mL/min and the collection time was about 10 minutes. After the conclusion of the collection step, the collection column was washed with 400 μL of water 4 times. Subsequently, the column was eluted with 400 μL of 70% isopropanol. Both washing solution and elution solution were collected and saved for MALDI-TOFMS analysis.

CHCA (α-Cyano-4-hydroxycinnamic acid) MALDI matrix was prepared in about 50% acetonitrile containing about 0.1% TFA (trifluoro acetic acid) at a concentration of about 10 mg/mL. About 1.5 μL of sample was mixed with about 0.5 μL CHCA matrix and applied to a MALDI plate. In each case, after the sample was sufficiently dried, the plate was inserted into an Axima-CFR time-of-flight instrument (Kratos Analytical by Shimadzu Biotech, Manchester, U.K.). MALDI-TOF mass spectra were obtained in linear mode with a 337 nm N2 laser (laser power, 90 arbitrary units) and all spectra were collected as an average of 200 profiles from 1000-15,000 m/z.

FIG. 8A shows MALDI mass spectra of the whole bacterial cell analysis of control sample, elution sample, and washing sample of *E. coli* (left), *Pseudomonas fluorescens* (middle), and *Yersinia rohdei* (right). The bacterial signatures are clearly seen in the elution samples but not in washing samples, indicating that the collection column was able to capture aerosolized bacteria. FIG. 8B shows (A) MALDI mass spectra of the whole virus MS2 analysis and (B) MALDI mass spectra of hot acid digestion analysis of virus MS2. The full mass of MS2 capsid protein (P03612) and its doubly charged ion were observed with MALDI-TOF MS. After hot acid digestion, the intact capsid protein (red dot) was observed as well as its digested peptides, which were characterized by MALDI-TOF MS.

The Abstract is provided to comply with 37 C.F.R. § 1.72(b), to allow the reader to determine quickly from a cursory inspection the nature and gist of the technical disclosure. It should not be used to interpret or limit the scope or meaning of the claims.

Although the present disclosure has been described in connection with the preferred form of practicing it, those of ordinary skill in the art will understand that many modifications can be made thereto without departing from the spirit of the present disclosure. Accordingly, it is not intended that the scope of the disclosure in any way be limited by the above description.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this disclosure is entitled. It should be understood that all actions may be expressed as a means for taking that action or as an element which causes that action. Similarly, each physical element disclosed should be understood to encompass a disclosure of the action which that physical element facilitates.

In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Further, the use of the transitional phrase "comprising" is used to maintain the "open-end" claims herein, according to traditional claim interpretation. Thus, unless the context requires otherwise, it should be understood that variations such as "comprises" or "comprising," are intended to imply the inclusion of a stated element or step or group of elements or steps, but not the exclusion of any other element or step or group of elements or steps. Such terms should be interpreted in their most expansive forms so as to afford the applicant the broadest coverage legally permissible.

REFERENCES

1. B. Bake, P. Larsson, G. Ljungkvist, E. Ljungström, and A-C Olin, "Exhaled particles and small airways," Respiratory Research (2019) 20:8.
2. Fennelly K. P., Martyny J. W., Fulton K. E., Orme I. M., Cave D. M., et al. (2004) Cough-generated aerosols of *Mycobacterium tuberculosis*: a new method to study infectiousness. Am J Respir Crit Care Med 169: 604-609.
3. Dina Hashoul and Hossam Haick, "Sensors for detecting pulmonary diseases from exhaled breath," Eur. Respir. Rev. 2019; 28: 190011.
4. Hunt, J., "Exhaled breath condensate: An evolving tool for noninvasive evaluation of lung disease," J. Allergy Clin. Immunol. 2002; 110:28-34.
5. Maria D. King, Andrew R. McFarland, "Bioaerosol Sampling with a Wetted Wall Cyclone: Cell Culturability and DNA Integrity of *Escherichia coli* Bacteria," Aerosol Sci. Technol., 46:82-93, 2012.
6. James J. McDevitt, Petros Koutrakis, Stephen T. Ferguson, Jack M. Wolfson, M. Patricia Fabian, Marco Martins, Jovan Pantelic, and Donald K. Milton, "Development and Performance Evaluation of an Exhaled-Breath Bioaerosol Collector for Influenza Virus," Aerosol Sci. Technol. 2013 Jan. 1; 47(4): 444-451.
7. Benjamin Patterson, Carl Morrow, Vinayak Singh, Atica Moosa, Melitta Gqada, Jeremy Woodward, Valerie Mizrahi, Wayne Bryden, Charles Call, Shwetak Patel, Digby Warner, Robin Wood, "Detection of *Mycobacterium tuberculosis* bacilli in bio-aerosols from untreated TB patients," Gates Open Research 2018, 1:11.
8. Wood R., Morrow C., Barry C. E., III, Bryden W. A., Call C. J., Hickey A. J., et al.: Real-Time Investigation of Tuberculosis Transmission: Developing the Respiratory Aerosol Sampling Chamber (RASC). PLoS One. 2016; 11(1): e0146658.
9. Rachel C. Wood, Angelique K. Luabeya, Kris M. Weigel, Alicia K. Wilbur, Lisa Jones-Engel, Mark Hatherill, and Gerard A. Cangelosi, "Detection of *Mycobacterium tuberculosis* DNA on the oral mucosa of tuberculosis patients," Sci. Rep. 5, 8668 (2015).
10. Fatima B. Wurie, Stephen D. Lawn, Helen Booth, Pam Sonnenberg, Andrew C. Hayward, "Bioaerosol production by patients with tuberculosis during normal tidal breathing: implications for transmission risk," Thorax 2016; 71: 549-554.

What is claimed is:

1. A breath sample collection system for diagnosis of at least one respiratory disease using exhaled breath, the system including:
    a breath collection element configured to receive an individual's face for collecting aerosolized particles including proteins in exhaled breath, wherein the breath collection element forms a tight-fit with the individual's face;
    a sample capture element including a packed bed column to selectively capture the aerosolized particles including proteins, wherein the sample capture element is removably and directly connected, without any interconnecting tubing, to a port disposed in the breath collection element proximate to the individual's chin when the breath collection element is positioned on the individual's face;
    a pump in fluid communication with the sample capture element and configured to draw exhaled breath into the sample capture element; and
    a humidifier disposed upstream of the sample capture element configured to humidify the packed bed column.

2. The system of claim 1, wherein the sample capture element is further configured to capture aerosolized particles including proteins associated with viruses including one or more of SARS-CoV, MERS-CoV, or SARS-CoV-2.

3. The system of claim 1, wherein the sample capture element is further configured to capture aerosolized particles including proteins that originate from the lower respiratory airways including one or more of serum albumin, keratins, glycoproteins, cystatin, dermcidin, or S100 proteins.

4. The system of claim 1, wherein a particle capture efficiency of the sample capture element is greater than 99%.

5. The system of claim 1, wherein the breath collection element includes one or more of a CPR rescue mask, a CPAP mask, or a ventilator mask.

6. The system of claim 1, wherein the packed bed column includes resin beads including C18 functional groups on the surface.

7. The system of claim 1, wherein the packed bed column includes heparin covalently linked to sepharose beads.

8. The system of claim 1, wherein the packed bed column includes solid particles having functional groups immobilized on the surface of the particles, wherein the functional groups include one or more of glycan, heparin, heparan sulfate, or carbohydrates including dextran.

9. The system of claim 1, wherein the pump includes a diaphragm pump.

10. The system of claim 1, further including a trap disposed between the sample capture element and the pump and configured to trap exhaled breath condensate (EBC) including one or more of water vapor, volatile organic components, or non-volatile organic components that pass through the packed bed.

11. The system of claim 10, wherein the trap is cooled to below ambient temperature.

12. A system for detecting aerosol particles including proteins in exhaled breath, the system including:
the breath sample collection system of claim 1;
a sample extraction system configured to extract the protein particles from the packed bed column;
a sample processing system including means for hot acid digestion of the protein particles extracted from the sample extraction system to generate a peptide sample characteristic of the captured proteins; and
a diagnostic device for analyzing the peptide sample characteristic of the captured proteins.

13. The system of claim 12, wherein the extraction system includes means to flush the packed bed column with one or more of about 12.5% acetic acid, about 5% TFA, about 5% formic acid, about 70% isopropanol, or about 10% HCl.

14. The system of claim 12, wherein the diagnostic device includes one or more of PCR, ELISA, rt-PCR, mass spectrometer (MS), LC-MS, MALDI-MS, ESI-MS, or MALDI-TOFMS.

15. A breath sample collection system for diagnosis of at least one respiratory disease using exhaled breath, the system including:
a mask configured to receive an individual's face for collecting aerosolized particles including proteins in exhaled breath, wherein the mask includes:
a stem; and
a port disposed below the stem and proximate to the individual's chin when the mask is positioned on the individual's face;
a HEPA filter removably and fluidly connected to the stem of the mask;
a sample capture element including a packed bed column to selectively capture the aerosolized particles including proteins in exhaled breath, wherein the sample capture element is removably and directly connected to the port without any interconnecting tubing;
a humidifier disposed upstream of the sample capture element configured to humidify the packed bed column; and
a pump in fluid communication with the sample capture element and configured to draw exhaled breath into the sample capture element.

16. The system of claim 15, wherein a particle capture efficiency of the sample capture element is greater than 99%.

17. The system of claim 15, wherein exhaled breath is pulled through the packed bed column by the pump at a flow rate of between about 200 ml/min and about 600 ml/min.

18. The system of claim 15, wherein the packed bed column includes resin beads including C18 functional groups on the surface.

19. The system of claim 15, wherein the packed bed column includes heparin covalently linked to sepharose beads.

20. The system of claim 15, wherein the packed bed column includes solid particles having functional groups immobilized on the surface of the particles, wherein the functional groups include one or more of glycan, heparin, heparan sulfate, or carbohydrates including dextran.

21. The system of claim 20, wherein the solid particles are packed between two porous polymeric frit discs.

* * * * *